(12) United States Patent
Robichaud et al.

(10) Patent No.: US 6,780,862 B2
(45) Date of Patent: Aug. 24, 2004

(54) ARYL AND AMINOARYL SUBSTITUTED SEROTONIN RECEPTOR AGONIST AND ANTAGONIST LIGANDS

(75) Inventors: Albert J. Robichaud, Landenberg, PA (US); Ian S. Mitchell, Philadelphia, PA (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 5 days.

(21) Appl. No.: 10/026,226

(22) Filed: Dec. 19, 2001

(65) Prior Publication Data

US 2003/0153576 A1 Aug. 14, 2003

Related U.S. Application Data

(60) Provisional application No. 60/256,821, filed on Dec. 20, 2000.

(51) Int. Cl.⁷ .................... C07D 241/36; C07D 487/04; A61K 31/498
(52) U.S. Cl. ........................ 514/250; 544/344
(58) Field of Search ........................... 544/344; 514/250

(56) References Cited

FOREIGN PATENT DOCUMENTS

| | | | |
|---|---|---|---|
| CA | 2097465 | * | 12/1993 |
| CA | 2153937 | | 2/1996 |
| EP | 0655440 | | 10/1994 |
| WO | WO 97/00871 | | 1/1997 |
| WO | WO 97/42183 | | 11/1997 |
| WO | WO 98/30546 | | 7/1998 |
| WO | WO 00/12475 | | 3/2000 |
| WO | WO 00/12481 | | 3/2000 |
| WO | WO 00/12482 | | 3/2000 |
| WO | WO 00/12510 | | 3/2000 |
| WO | WO 00/44753 | * | 8/2000 |

* cited by examiner

*Primary Examiner*—Deepak Rao
(74) *Attorney, Agent, or Firm*—Sammy G. Duncan, Jr.; Maureen P. O'Brien

(57) ABSTRACT

The present invention is directed to certain novel compounds represented by structural Formula (I):

$$S^{ag}\text{-}T^{ag} \quad \quad \text{(I)}$$

or a pharmaceutically acceptable salt thereof, wherein $S^{ag}$ and $T^{ag}$ are described herein. The invention is also concerned with pharmaceutical formulations comprising these novel compounds as active ingredients and the use of the novel compounds and their formulations in the treatment of certain disorders. The compounds of this invention are serotonin agonists and antagonists and are useful in the control or prevention of central nervous system disorders including obesity, anxiety, depression, psychosis, schizophrenia, sleep and sexual disorders, migraine and other conditions associated with cephalic pain, social phobias, and gastrointestinal disorders such as dysfunction of the gastrointestinal tract motility.

15 Claims, No Drawings

ARYL AND AMINOARYL SUBSTITUTED SEROTONIN RECEPTOR AGONIST AND ANTAGONIST LIGANDS

FIELD OF THE INVENTION

The present invention is directed to certain novel compounds represented by structural Formula (I):

$$S^{ag}\text{-}T^{ag} \quad\quad\quad (I)$$

or a pharmaceutically acceptable salt thereof, wherein $S^{ag}$ and $T^{ag}$ are described herein. The invention is also concerned with pharmaceutical formulations comprising these novel compounds as active ingredients and the use of the novel compounds and their formulations in the treatment of certain disorders. The compounds of this invention are serotonin agonists and antagonists and are useful in the control or prevention of central nervous system disorders including obesity, anxiety, depression, psychosis, schizophrenia, sleep and sexual disorders, migraine and other conditions associated with cephalic pain, social phobias, and gastrointestinal disorders such as dysfunction of the gastrointestinal tract motility.

BACKGROUND OF THE INVENTION

There exists a substantial correlation for the relationship between 5-HT2 receptor modulation and a variety of diseases and therapies. To date, three subtypes of the 5-HT2 receptor class have been identified, 5-HT2A, 5-HT2B, and 5-HT2C. Prior to the early 1990's the 5-HT2C and 5-HT2A receptors were referred to as 5-HT1C and 5-HT2, respectively.

The agonism or antagonism of 5-HT2 receptors, either selectively or nonselectively, has been associated with the treatment of various central nervous system (CNS) disorders. Ligands possessing affinity for the 5-HT2 receptors have been shown to have numerous physiological and behavioral effects (Trends in Pharmacological Sciences, 11, 181, 1990). In the recent past the contribution of serotonergic activity to the mode of action of antidepressant drugs has been well documented. Compounds that increase the overall basal tone of serotonin in the CNS have been successfully developed as antidepressants. The serotonin selective reuptake inhibitors (SSRI) function by increasing the amount of serotonin present in the nerve synapse. These breakthrough treatments, however, are not without side effects and suffer from delayed onset of action (Leonard, J. Clin. Psychiatry, 54(suppl), 3, 1993). Due to the mechanism of action of the SSRIs, they effect the activity of a number of serotonin receptor subtypes. This non-specific modulation of the serotonin family of receptors most likely plays a significant role in the side effect profile. In addition, these compounds often have a high affinity for a number of the serotonin receptors as well as a multitude of other monoamine neurotransmitters and nuisance receptors. Removing some of the receptor cross reactivity would allow for the examination and possible development of potent therapeutic ligands with an improved side effect profile.

There is ample evidence to support the role of selective 5-HT2 receptor ligands in a number of disease therapies. Modulation of 5-HT2 receptors has been associated with the treatment of schizophrenia and psychoses (Ugedo, L., et.al., Psychopharmacology, 98, 45, 1989). Mood, behavior and hallucinogenesis can be affected by 5-HT2 receptors in the limbic system and cerebral cortex. 5-HT2 receptor modulation in the hypothalamus can influence appetite, thermoregulation, sleep, sexual behavior, motor activity, and neuroendocrine function (Hartig, P., et.al., Annals New York Academy of Science, 149, 159). There is also evidence indicating that 5-HT2 receptors mediate hypoactivity, effect feeding in rats, and mediate penile erections (Pyschopharmacology, 101, 57, 1990).

Compounds exhibiting selectivity for the 5-HT2B receptor are useful in treating conditions such as tachygastria, hypermotility associated with irritable bowel disorder, constipation, dyspepsia, and other peripherally mediated conditions.

5-HT2A antagonists have been shown to be effective in the treatment of schizophrenia, anxiety, depression, and migraines (Koek, W., Neuroscience and Behavioral reviews, 16, 95, 1996). Aside from the beneficial antipsychotic effects, classical neuroleptic are frequently responsible for eliciting acute extrapyramidal side effects and neuroendocrine disturbances. These compounds generally possess significant dopamine D2 receptor affinity (as well as other nuisance receptor affinity) which frequently is associated with extra pyramidal symptoms and tardive dyskinesia, thus detracting from their efficacy as front line treatments in schizophrenia and related disorders. Compounds possessing a more favorable selectivity profile would represent a possible improvement for the treatment of CNS disorders.

The following patent applications/publications disclose compounds useful as serotonin agonists and antagonists: 1) WO 00/12482; 2) WO 00/12481; 3) WO 00/44753; 4) WO 00/12510;5) WO 00/12475; 6) WO 97/42183; 7) WO 98/30546; 8) WO 97/00871;9) CA 2,153,937; 10) EP 0655440; and 11) CA 2,097,465.

None of the above references suggest or disclose the compounds of the present invention.

There remains a need to discover new compounds useful as serotonin agonists and antagonists which are useful in the control or prevention of central nervous system disorders. As such, the present invention discloses novel compounds which are of low molecular weight, useful as serotonin agonists and antagonists, and provide good in vitro potency.

SUMMARY OF THE INVENTION

One object of the present invention is to provide novel compounds which are useful as agonists or antagonists of 5-HT2 receptors, more specifically 5-HT2A and 5-HT2C receptors, or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating central nervous system disorders including obesity, anxiety, depression, psychosis, schizophrenia, sleep and sexual disorders, migraine and other conditions associated with cephalic pain, social phobias, and gastrointestinal disorders such as dysfunction of the gastrointestinal tract motility comprising administering to a host in need of such treatment a therapeutically effective amount of at least one of the compounds of the present invention or a pharmaceutically acceptable salt or prodrug form thereof. More specifically, the present invention provides a method for treating obesity anxiety, depression, or schizophrenia.

These and other objects, which will become apparent during the following detailed description, have been achieved by the inventors' discovery that compounds of Formula (I):

$$S^{ag}\text{-}T^{ag} \qquad (I)$$

or a pharmaceutically acceptable salt or prodrug form thereof, wherein $S^{ag}$ and $T^{ag}$ are defined below, are effective agonists or antagonists of 5-HT2 receptors.

DETAILED DESCRIPTION OF THE INVENTION

Thus, in a first embodiment, the present invention provides a novel compound of Formula (I):

$$S^{ag}\text{-}T^{ag} \qquad (I)$$

or a stereoisomer or a pharmaceutically acceptable salt form thereof, wherein:

$S^{ag}$ is $R^A$ or $R^B$;
wherein
$R^A$ is $-NR^{12}R^{13}$;
$R^B$ is $-NR^{12}R^{13}$ or aryl substituted with 0–5 $R^{33}$; and
aryl is phenyl, pyridyl, or naphthyl; and
$T^{ag}$ is a heterocyclic serotonin receptor ligand template selected from:

1)
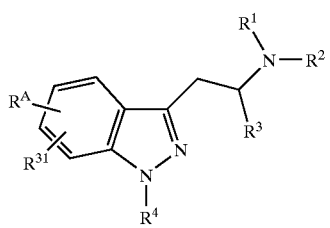

2)
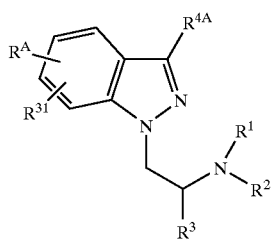

3)
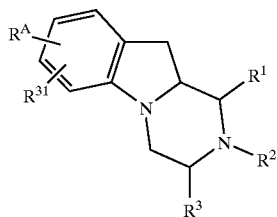

4)
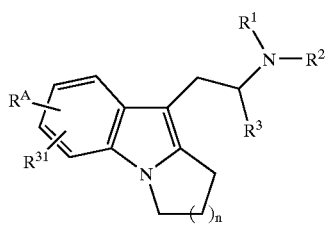

5)
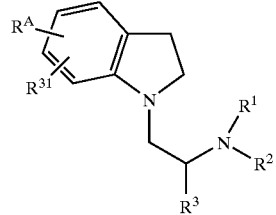

6)
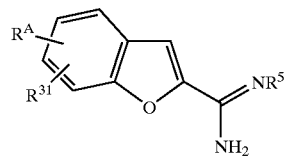

7)
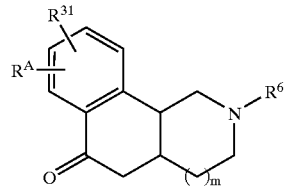

8)
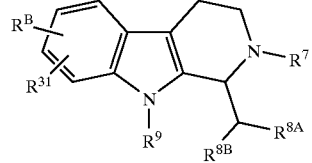

9)
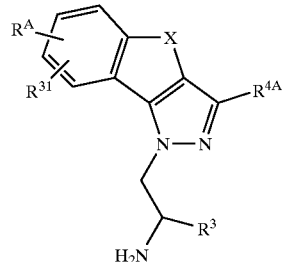

10)
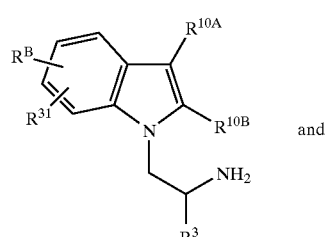

and

11)
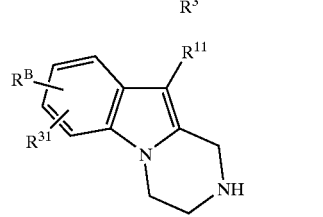

wherein:
X is $-CH=CH-$, $-CR^1R^2-$, or $-CR^1R^2-CR^1R^2-$;
n is 1, 2, or 3;
m is 0 or 1;
$R^1$ is H or $C_{1-4}$ alkyl;

$R^2$ is H or $C_{1-4}$ alkyl;

$R^3$ is H or $C_{1-4}$ alkyl;

$R^4$ is H or $C_{1-4}$ alkyl;

$R^{4A}$ is H, $C_{1-4}$ alkyl or $C_{1-4}$ alkyloxy;

$R^5$ is H, —OH or $C_{1-4}$ alkyloxy;

$R^6$ is H, $C_{1-6}$ alkyl, $C_{2-6}$ alkenyl, or $C_{1-2}$ alkyl substituted with $R^{6A}$;

$R^{6A}$ is phenyl, cyclopropyl, cyclobutyl, cyclopentyl or cyclohexyl;

$R^7$ is H, $C_{1-6}$ alkyl, $C_{2-6}$ alkenyl, cyclopropyl, cyclobutyl, cyclopentyl or cyclohexyl;

$R^{8A}$ is a 5–10 membered heterocyclic ring system containing from 1–3 heteroatoms selected from the group benzimidazolyl, benzimidazolinyl, benztriazolyl, benzisoxazolyl, benzisoxazolinyl, benzoxazolyl, benzoxazolinyl, benzthiazolyl, benzisothiazolyl, indolyl, indolinyl, isoindolinyl, indazolyl, isatinoyl, isoxazolopyridinyl, isothiazolopyridinyl, thiazolopyridinyl, oxazolopyridinyl, oxindolyl, oxazolidinyl, imidazolopyridinyl, and pyrazolopyridinyl;
  wherein said heterocyclic ring system is substituted with 0–2 $R^{41}$;

$R^{8B}$ is H, $C_{1-6}$ alkyl, $C_{2-6}$ alkenyl, cyclopropyl, cyclobutyl, cyclopentyl or cyclohexyl;

$R^9$ is H, $C_{1-6}$ alkyl, $C_{2-6}$ alkenyl, cyclopropyl, cyclobutyl, cyclopentyl or cyclohexyl;

$R^{10A}$ and $R^{10b}$, at each occurrence, are independently selected from
  H, —OH, halo, —CF$_3$, —OCF$_3$, $C_{1-6}$ alkyl, $C_{1-6}$ alkyloxy-, cyclopropyl, cyclobutyl, cyclopentyl or cyclohexyl;

$R^{11}$ is H, $C_{1-6}$ alkoxy or $C_{1-6}$ alkyl-S—;

$R^{12}$ is aryl substituted with 0–5 $R^{33}$;

$R^{13}$ is selected from
  H, $C_{1-4}$ alkyl, $C_{2-4}$ alkenyl, and $C_{2-4}$ alkynyl;
  alternatively, $R^{12}$ and $R^{13}$ join to form a 5- or 6-membered ring optionally substituted with —O— or —N(R$^{14}$)—;

alternatively, $R^{12}$ and $R^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;

$R^{14}$ is H or $C_{1-4}$ alkyl;

$R^{16}$, at each occurrence, is independently selected from H, OH, halo, CN, NO$_2$, CF$_3$, SO$_2$R$^{45}$, NR$^{46}$R$^{47}$, —C(=O) H, $C_{1-4}$ alkyl, $C_{2-4}$ alkenyl, $C_{2-4}$ alkynyl, $C_{1-4}$ haloalkyl, $C_{1-3}$ haloalkyl-oxy-, and $C_{1-3}$ alkyloxy-;

$R^{31}$, at each occurrence, is independently selected from H, —OH, halo, —CN, —NO$_2$, —CF$_3$, —OCF$_3$, $C_{1-6}$ alkyl, $C_{1-4}$ alkyl-C(=O)—, $C_{1-4}$ alkyloxy-, $C_{1-4}$ alkylthio-, $C_{1-4}$ alkyl-S(=O)—, and $C_{1-4}$ alkyl-SO$_2$—;

$R^{33}$, at each occurrence, is independently selected from H, OH, halo, CN, NO$_2$, CF$_3$, SO$_2$R$^{45}$, NR$^{46}$R$^{47}$, —C(=O) H, phenyl, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, 1–4 alkyloxy-, $C_{1-4}$ alkylthio-, $C_{1-4}$ alkyl-C(=O)—, $C_{1-4}$ alkyl-C(=O)NH—, $C_{1-4}$ alkyl-OC(=O)—, $C_{1-4}$ alkyl-C(=O)O—, $C_{3-6}$ cycloalkyl-oxy-, $C_{3-6}$ cycloalkylmethyl-oxy-;
$C_{1-6}$ alkyl substituted with OH, methoxy, ethoxy, propoxy, butoxy, —SO$_2$R$^{45}$, —NR$^{46}$R$^{47}$, NR$^{46}$R$^{47}$C(=O)—, or (C$_{1-4}$ alkyl)CO$_2$—; and $C_{2-6}$ alkenyl substituted with OH, methoxy, ethoxy, propoxy, butoxy, —SO$_2$R$^{45}$, —NR$^{46}$R$^{47}$, NR$^{46}$R$^{47}$C(=O)—, or (C$_{1-4}$ alkyl)CO$_2$—;

$R^{41}$, at each occurrence, is independently selected from H, —OH, F, Cl, —CF$_3$, —OCF$_3$, methyl, ethyl, methoxy, and ethoxy;

$R^{45}$ is $C_{1-4}$ alkyl;

$R^{46}$, at each occurrence, is independently selected from H and $C_{1-4}$ alkyl; and $R^{47}$, at each occurrence, is independently selected from H, $C_{1-4}$ alkyl, —C(=O)NH(C$_{1-4}$ alkyl), —SO$_2$(C$_{1-4}$ alkyl), —C(=O)O(C$_{1-4}$ alkyl), —C(=O)(C$_{1-4}$ alkyl), and —C(=O)H.

[2] In an another embodiment, the present invention provides a novel compound of Formula (I) wherein:

$R^A$ is —NR$^{12}$R$^{13}$;

$R^B$ is —NR$^{12}$R$^{13}$;

phenyl- substituted with 0–5 fluoro;

naphthyl- substituted with 0–3 $R^{33}$;

2-(H$_3$CCH$_2$C(=O))-phenyl- substituted with $R^{33}$;

2-(H$_3$CC(=O))-phenyl- substituted with $R^{33}$;

2-(HC(=O))-phenyl- substituted with $R^{33}$;

2-(H$_3$CCH(OH))-phenyl- substituted with $R^{33}$;

2-(H$_3$CCH$_2$CH(OH))-phenyl- substituted with $R^{33}$;

2-(HOCH$_2$)-phenyl- substituted with $R^{33}$;

2-(HOCH$_2$CH$_2$)-phenyl- substituted with $R^{33}$;

2-(H$_3$COCH$_2$)-phenyl- substituted with $R^{33}$;

2-(H$_3$COCH$_2$CH$_2$)-phenyl- substituted with $R^{33}$;

2-(H$_3$CCH(OMe))-phenyl- substituted with $R^{33}$;

2-(H$_3$COC(=O))-phenyl- substituted with $R^{33}$;

2-(HOCH$_2$CH=CH)-phenyl- substituted with $R^{33}$;

2-((MeOC=O)CH=CH)-phenyl- substituted with $R^{33}$;

2-(methyl)-phenyl- substituted with $R^{33}$;

2-(ethyl)-phenyl- substituted with $R^{33}$;

2-(i-propyl)-phenyl- substituted with $R^{33}$;

2-(F$_3$C)-phenyl- substituted with $R^{33}$;

2-(NC)-phenyl- substituted with $R^{33}$;

2-(H$_3$CO)-phenyl- substituted with $R^{33}$;

2-(fluoro)-phenyl- substituted with $R^{33}$;

2-(chloro)-phenyl- substituted with $R^{33}$;

3-(NC)-phenyl- substituted with $R^{33}$;

3-(H$_3$CO)-phenyl- substituted with $R^{33}$;

3-(fluoro)-phenyl- substituted with $R^{33}$;

3-(chloro)-phenyl- substituted with $R^{33}$;

4-(NC)-phenyl- substituted with $R^{33}$;

4-(fluoro)-phenyl- substituted with $R^{33}$;

4-(chloro)-phenyl- substituted with $R^{33}$;

4-(H$_3$CS)-phenyl- substituted with $R^{33}$;

4-(H$_3$CO)-phenyl- substituted with $R^{33}$;

4-(ethoxy)-phenyl- substituted with $R^{33}$;

4-(i-propoxy)-phenyl- substituted with $R^{33}$;

4-(i-butoxy)-phenyl- substituted with $R^{33}$;

4-(H$_3$CCH$_2$CH$_2$C(=O))-phenyl- substituted with $R^{33}$;

4-((H$_3$C)$_2$CHC(=O))-phenyl- substituted with $R^{33}$;

4-(H$_3$CCH$_2$C(=O))-phenyl- substituted with $R^{33}$;

4-(H$_3$CC(=O))-phenyl- substituted with $R^{33}$;

4-(H$_3$CCH$_2$CH$_2$CH(OH))-phenyl- substituted with $R^{33}$;

4-((H$_3$C)$_2$CHCH(OH))-phenyl- substituted with $R^{33}$;

4-(H$_3$CCH$_2$CH(OH))-phenyl- substituted with $R^{33}$;

4-(H$_3$CCH(OH))-phenyl- substituted with $R^{33}$;

4-(cyclopropyloxy)-phenyl- substituted with $R^{33}$;

4-(cyclobutyloxy)-phenyl- substituted with $R^{33}$; or 4-(cyclopentyloxy)-phenyl- substituted with $R^{33}$;

$R^{12}$ is selected from
- phenyl- substituted with 0–5 fluoro;
- naphthyl- substituted with 0–3 $R^{33}$;
- 2-($H_3CCH_2C(=O)$)-phenyl- substituted with $R^{33}$;
- 2-($H_3CC(=O)$)-phenyl- substituted with $R^{33}$;
- 2-($HC(=O)$)-phenyl- substituted with $R^{33}$;
- 2-($H_3CCH(OH)$)-phenyl- substituted with $R^{33}$;
- 2-($H_3CCH_2CH(OH)$)-phenyl- substituted with $R^{33}$;
- 2-($HOCH_2$)-phenyl- substituted with $R^{33}$;
- 2-($HOCH_2CH_2$)-phenyl- substituted with $R^{33}$;
- 2-($H_3COCH_2$)-phenyl- substituted with $R^{33}$;
- 2-($H_3COCH_2CH_2$)-phenyl- substituted with $R^{33}$;
- 2-($H_3CCH(OMe)$)-phenyl- substituted with $R^{33}$;
- 2-($H_3COC(=O)$)-phenyl- substituted with $R^{33}$;
- 2-($HOCH_2CH=CH$)-phenyl- substituted with $R^{33}$;
- 2-(($MeOC=O)CH=CH$)-phenyl- substituted with $R^{33}$;
- 2-(methyl)-phenyl- substituted with $R^{33}$;
- 2-(ethyl)-phenyl- substituted with $R^{33}$;
- 2-(i-propyl)-phenyl- substituted with $R^{33}$;
- 2-($F_3C$)-phenyl- substituted with $R^{33}$;
- 2-(NC)-phenyl- substituted with $R^{33}$;
- 2-($H_3CO$)-phenyl- substituted with $R^{33}$;
- 2-(fluoro)-phenyl- substituted with $R^{33}$;
- 2-(chloro)-phenyl- substituted with $R^{33}$;
- 3-(NC)-phenyl- substituted with $R^{33}$;
- 3-($H_3CO$)-phenyl- substituted with $R^{33}$;
- 3-(fluoro)-phenyl- substituted with $R^{33}$;
- 3-(chloro)-phenyl- substituted with $R^{33}$;
- 4-(NC)-phenyl- substituted with $R^{33}$;
- 4-(fluoro)-phenyl- substituted with $R^{33}$;
- 4-(chloro)-phenyl- substituted with $R^{33}$;
- 4-($H_3CS$)-phenyl- substituted with $R^{33}$;
- 4-($H_3CO$)-phenyl- substituted with $R^{33}$;
- 4-(ethoxy)-phenyl- substituted with $R^{33}$;
- 4-(i-propoxy)-phenyl- substituted with $R^{33}$;
- 4-(i-butoxy)-phenyl- substituted with $R^{33}$;
- 4-($H_3CCH_2CH_2C(=O)$)-phenyl- substituted with $R^{33}$;
- 4-(($H_3C)_2CHC(=O)$)-phenyl- substituted with $R^{33}$;
- 4-($H_3CCH_2C(=O)$)-phenyl- substituted with $R^{33}$;
- 4-($H_3CC(=O)$)-phenyl- substituted with $R^{33}$;
- 4-($H_3CCH_2CH_2CH(OH)$)-phenyl- substituted with $R^{33}$;
- 4-(($H_3C)_2CHCH(OH)$)-phenyl- substituted with $R^{33}$;
- 4-($H_3CCH_2CH(OH)$)-phenyl- substituted with $R^{33}$;
- 4-($H_3CCH(OH)$)-phenyl- substituted with $R^{33}$;
- 4-(cyclopropyloxy)-phenyl- substituted with $R^{33}$;
- 4-(cyclobutyloxy)-phenyl- substituted with $R^{33}$; and
- 4-(cyclopentyloxy)-phenyl- substituted with $R^{33}$;

$R^{13}$ is H, methyl, or ethyl;

alternatively, $R^{12}$ and $R^{13}$ join to form a 5- or 6-membered ring selected from pyrrolyl, pyrrolidinyl, imidazolyl, piperidinyl, piperizinyl, methylpiperizinyl, and morpholinyl;

alternatively, $R^{12}$ and $R^{13}$ when attached to N may be combined to form a 9- or 10-membered bicyclic heterocyclic ring system containing from 1–3 heteroatoms selected from the group consisting of N, O, and S; wherein said bicyclic heterocyclic ring system is selected from indolyl, indolinyl, indazolyl, benzimidazolyl, benzimidazolinyl, and benztriazolyl; wherein said bicyclic heterocyclic ring system is substituted with 0–1 $R^{16}$;

$R^{16}$, at each occurrence, is independently selected from H, OH, F, Cl, CN, $NO_2$, methyl, ethyl, methoxy, ethoxy, trifluoromethyl, and trifluoromethoxy; and $R^{31}$, at each occurrence, is independently selected from H, —OH, F, Cl, —$CF_3$, —$OCF_3$, methyl, ethyl, methyl-$C(=O)$—, ethyl-$C(=O)$—, methoxy, ethoxy, methylthio-, ethylthio-, methyl-$S(=O)$—, ethyl-$S(=O)$—, methyl-$SO_2$—, and ethyl-$SO_2$—;

$R^{33}$, at each occurrence, is independently selected from H, F, Cl, —$CH_3$, —$OCH_3$, —$CF_3$, —$OCF_3$, —CN, and —$NO_2$.

[3] In a preferred embodiment, the present invention provides a novel compound of Formula (I) wherein:

$R^A$ is selected from
- phenyl-NH—, (1-naphthyl)-NH—,
- (2-naphthyl)-NH—, (2-[1,1'-biphenyl])-NH—,
- (3-[1,1'-biphenyl])-NH—, (4-[1,1'-biphenyl])-NH—,
- (2-F-phenyl)-NH—, (2-Cl-phenyl)-NH—,
- (2-$CF_3$-phenyl)-NH—, (2-$CH_3$-phenyl)-NH—,
- (2-OMe-phenyl)-NH—, (2-CN-phenyl)-NH—,
- (2-$OCF_3$-phenyl)-NH—, (2-SMe-phenyl)-NH—,
- (3-F-phenyl)-NH—, (3-Cl-phenyl)-NH—,
- (3-$CF_3$-phenyl)-NH—, (3-$CH_3$-phenyl)-NH—,
- (3-OMe-phenyl)-NH—, (3-CN-phenyl)-NH—,
- (3-$OCF_3$-phenyl)-NH—, (3-SMe-phenyl)-NH—,
- (4-F-phenyl)-NH—, (4-Cl-phenyl)-NH—,
- (4-$CF_3$-phenyl)-NH—, (4-$CH_3$-phenyl)-NH—,
- (4-OMe-phenyl)-NH—, (4-CN-phenyl)-NH—,
- (4-$OCF_3$-phenyl)-NH—, (4-SMe-phenyl)-NH—,
- (2,3-diCl-phenyl)-NH—, (2,4-diCl-phenyl)-NH—,
- (2,5-diCl-phenyl)-NH—, (2,6-diCl-phenyl)-NH—,
- (3,4-diCl-phenyl)-NH—, (3,5-diCl-phenyl)-NH—,
- (2,3-diF-phenyl)-NH—, (2,4-diF-phenyl)-NH—,
- (2,5-diF-phenyl)-NH—, (2,6-diF-phenyl)-NH—,
- (3,4-diF-phenyl)-NH—, (3,5-diF-phenyl)-NH—,
- (2,3-di$CH_3$-phenyl)-NH—, (2,4-di$CH_3$-phenyl)-NH—,
- (2,5-di$CH_3$-phenyl)-NH—, (2,6-di$CH_3$-phenyl)-NH—,
- (3,4-di$CH_3$-phenyl)-NH—, (3,5-di$CH_3$-phenyl)-NH—,
- (2,3-di$CF_3$-phenyl)-NH—, (2,4-di$CF_3$-phenyl)-NH—,
- (2,5-di$CF_3$-phenyl)-NH—, (2,6-di$CF_3$-phenyl)-NH—,
- (3,4-di$CF_3$-phenyl)-NH—, (3,5-di$CF_3$-phenyl)-NH—,
- (2,3-diOMe-phenyl)-NH—, (2,4-diOMe-phenyl)-NH—,
- (2,5-diOMe-phenyl)-NH—, (2,6-diOMe-phenyl)-NH—,
- (3,4-diOMe-phenyl)-NH—, (3,5-diOMe-phenyl)-NH—,
- (2-F-3-Cl-phenyl)-NH—, (2-F-4-Cl-phenyl)-NH—,
- (2-F-5-Cl-phenyl)-NH—, (2-F-6-Cl-phenyl)-NH—,
- (2-F-3-$CH_3$-phenyl)-NH—, (2-F-4-$CH_3$-phenyl)-NH—,
- (2-F-5-$CH_3$-phenyl)-NH—, (2-F-6-$CH_3$-phenyl)-NH—,
- (2-F-3-$CF_3$-phenyl)-NH—, (2-F-4-$CF_3$-phenyl)-NH—,
- (2-F-5-$CF_3$-phenyl)-NH—, (2-F-6-$CF_3$-phenyl)-NH—,
- (2-F-3-OMe-phenyl)-NH—, (2-F-4-OMe-phenyl)-NH—,
- (2-F-5-OMe-phenyl)-NH—, (2-F-6-OMe-phenyl)-NH—,
- (2-Cl-3-F-phenyl)-NH—, (2-Cl-4-F-phenyl)-NH—,
- (2-Cl-5-F-phenyl)-NH—, (2-Cl-6-F-phenyl)-NH—,
- (2-Cl-3-$CH_3$-phenyl)-NH—, (2-Cl-4-$CH_3$-phenyl)-NH—,
- (2-Cl-5-$CH_3$-phenyl)-NH—, (2-Cl-6-$CH_3$-phenyl)-NH—,
- (2-Cl-3-$CF_3$-phenyl)-NH—, (2-Cl-4-$CF_3$-phenyl)-NH—,
- (2-Cl-5-$CF_3$-phenyl)-NH—, (2-Cl-6-$CF_3$-phenyl)-NH—,
- (2-Cl-3-OMe-phenyl)-NH—, (2-Cl-4-OMe-phenyl)-NH—, (2-Cl-5-OMe-phenyl)-NH—, (2-Cl-6-OMe-phenyl)-NH—,
(2-CH$_3$-3-F-phenyl)-NH—, (2-CH$_3$-4-F-phenyl)-NH—,
(2-CH$_3$-5-F-phenyl)-NH—, (2-CH$_3$-6-F-phenyl)-NH—,
(2-CH$_3$-3-Cl-phenyl)-NH—, (2-CH$_3$-4-Cl-phenyl)-NH—,
(2-CH$_3$-5-Cl-phenyl)-NH—, (2-CH$_3$-6-C$_1$-phenyl)-NH—,
(2-CH$_3$-3-CF$_3$-phenyl)-NH—, (2-CH$_3$-4-CF$_3$-phenyl)-NH—,
(2-CH$_3$-5-CF$_3$-phenyl)-NH—, (2-CH$_3$-6-CF$_3$-phenyl)-NH—,
(2-CH$_3$-3-OMe-phenyl)-NH—, (2-CH$_3$-4-OMe-phenyl)-NH—,
(2-CH$_3$-5-OMe-phenyl)-NH—, (2-CH$_3$-6-OMe-phenyl)-NH—,
(2-CF$_3$-3-F-phenyl)-NH—, (2-CF$_3$-4-F-phenyl)-NH—,
(2-CF$_3$-5-F-phenyl)-NH—, (2-CF$_3$-6-F-phenyl)-NH—,
(2-CF$_3$-3-Cl-phenyl)-NH—, (2-CF$_3$-4-Cl-phenyl)-NH—,
(2-CF$_3$-5-Cl-phenyl)-NH—, (2-CF$_3$-6-Cl-phenyl)-NH—,
(2-CF$_3$-3-CH$_3$-phenyl)-NH—, (2-CF$_3$-4-CH$_3$-phenyl)-NH—,
(2-CH$_3$-5-CF$_3$-phenyl)-NH—, (2-CF$_3$-6-CH$_3$-phenyl)-NH—,
(2-CF$_3$-3-OMe-phenyl)-NH—, (2-CF$_3$-4-OMe-phenyl)-NH—,
(2-CF$_3$-5-OMe-phenyl)-NH—, (2-CF$_3$-6-OMe-phenyl)-NH—,
(2-OMe-3-F-phenyl)-NH—, (2-OMe-4-F-phenyl)-NH—,
(2-OMe-5-F-phenyl)-NH—, (2-OMe-6-F-phenyl)-NH—,
(2-OMe-3-Cl-phenyl)-NH—, (2-OMe-4-Cl-phenyl)-NH—,
(2-OMe-5-Cl-phenyl)-NH—, (2-OMe-6-Cl-phenyl)-NH—,
(2-OMe-3-CH$_3$-phenyl)-NH—, (2-OMe-4-CH$_3$-phenyl)-NH—,
(2-OMe-5-CH$_3$-phenyl)-NH—, (2-OMe-6-CH$_3$-phenyl)-NH—,
(2-OMe-3-CF$_3$-phenyl)-NH—, (2-OMe-4-CF$_3$-phenyl)-NH—,
(2-OMe-5-CF$_3$-phenyl)-NH—, (2-OMe-6-CF$_3$-phenyl)-NH—,
(3-CF$_3$-4-Cl-phenyl)-NH—, (3-CF$_3$-4-C(O)CH$_3$-phenyl)-NH—,
(2,3,5-triCl-phenyl)-NH—, (3-CH$_3$-4-CO$_2$Me-phenyl)-NH—, and
(3-CHO-4-OMe-phenyl)-NH—;
R$^B$ is selected from
2-chlorophenyl, 2-fluorophenyl, 2-bromophenyl, 2-cyanophenyl, 2-methylphenyl, 2-trifluoromethylphenyl,
2-methoxyphenyl, 2-trifluoromethoxyphenyl,
3-chlorophenyl, 3-fluorophenyl, 3-bromophenyl, 3-cyanophenyl, 3-methylphenyl, 3-ethylphenyl, 3-propylphenyl, 3-isopropylphenyl, 3-butylphenyl, 3-trifluoromethylphenyl, 3-methoxyphenyl, 3-isopropoxyphenyl, 3-trifluoromethoxyphenyl, 3-thiomethoxyphenyl,
4-chlorophenyl, 4-fluorophenyl, 4-bromophenyl, 4-cyanophenyl, 4-methylphenyl, 4-ethylphenyl, 4-propylphenyl, 4-isopropylphenyl, 4-butylphenyl, 4-trifluoromethylphenyl, 4-methoxyphenyl, 4-isopropoxyphenyl, 4-trifluoromethoxyphenyl, 4-thiomethoxyphenyl,
2,3-dichlorophenyl, 2,3-difluorophenyl, 2,3-dimethylphenyl, 2,3-ditrifluoromethylphenyl, 2,3-dimethoxyphenyl, 2,3-ditrifluoromethoxyphenyl,
2,4-dichlorophenyl, 2,4-difluorophenyl, 2,4-dimethylphenyl, 2,4-ditrifluoromethylphenyl, 2,4-dimethoxyphenyl, 2,4-ditrifluoromethoxyphenyl,
2,5-dichlorophenyl, 2,5-difluorophenyl, 2,5-dimethylphenyl, 2,5-ditrifluoromethylphenyl, 2,5-dimethoxyphenyl, 2,5-ditrifluoromethoxyphenyl,
2,6-dichlorophenyl, 2,6-difluorophenyl, 2,6-dimethylphenyl, 2,6-ditrifluoromethylphenyl, 2,6-dimethoxyphenyl, 2,6-ditrifluoromethoxyphenyl,
3,4-dichlorophenyl, 3,4-difluorophenyl, 3,4-dimethylphenyl, 3,4-ditrifluoromethylphenyl, 3,4-dimethoxyphenyl, 3,4-ditrifluoromethoxyphenyl,
2,4,6-trichlorophenyl, 2,4,6-trifluorophenyl, 2,4,6-trimethylphenyl, 2,4,6-tritrifluoromethylphenyl, 2,4,6-trimethoxyphenyl, 2,4,6-tritrifluoromethoxyphenyl,
2-chloro-4-CF$_3$-phenyl, 2-fluoro-3-chloro-phenyl, 2-chloro-4-CF$_3$-phenyl, 2-chloro-4-methoxy-phenyl, 2-methoxy-4-isopropyl-phenyl, 2-CF$_3$-4-methoxy-phenyl,
2-methyl-4-methoxy-5-fluoro-phenyl,
2-methyl-4-methoxy-phenyl, 2-chloro-4-CF$_3$O-phenyl, 2,4,5-trimethyl-phenyl, 2-methyl-4-chloro-phenyl, 4-acetylphenyl, 3-acetamidophenyl, 2-naphthyl;
2-Me-5-F-phenyl, 2-F-5-Me-phenyl, 2-MeO-5-F-phenyl,
2-Me-3-Cl-phenyl, 3-NO$_2$-phenyl, 2-NO$_2$-phenyl,
2-Cl-3-Me-phenyl, 2-Me-4-EtO-phenyl, 2-Me-4-F-phenyl,
2-Cl-6-F-phenyl, 2-Cl-4-(CHF$_2$)O-phenyl,
2,4-diMeO-6-F-phenyl, 2-CF$_3$-6-F-phenyl,
2-MeS-phenyl, 2,6-diCl-4-MeO-phenyl,
2,3,4-triF-phenyl, 2,6-diF-4-Cl-phenyl,
2,3,4,6-tetraF-phenyl, 2,3,4,5,6-pentaF-phenyl,
2-CF$_3$-4-EtO-phenyl, 2-CF$_3$-4-iPrO-phenyl,
2-CF$_3$-4-Cl-phenyl, 2-CF$_3$-4-F-phenyl, 2-Cl-4-EtO-phenyl,
2-Cl-4-iPrO-phenyl, 2-Et-4-MeO-phenyl,
2-CHO-4-MeO-phenyl, 2-CH$_3$CH(OH)-4-MeO-phenyl,
2-CH$_3$CH(OH)-4-F-phenyl, 2-CH$_3$CH(OH)-4-Cl-phenyl,
2-CH$_3$CH(OH)-4-Me-phenyl, 2-CH$_3$CH(OMe)-4-MeO-phenyl,
2-CH$_3$C(=O)-4-MeO-phenyl, 2-CH$_3$C(=O)-4-F-phenyl,
2-CH$_3$C(=O)-4-Cl-phenyl, 2-CH$_3$C(=O)-4-Me-phenyl,
2-H$_2$C(OH)-4-MeO-phenyl, 2-H$_2$C(OMe)-4-MeO-phenyl,
2-H$_3$CCH$_2$CH(OH)-4-MeO-phenyl, 2-H$_3$CCH$_2$C(=O)-4-MeO-phenyl,
2-CH$_3$CO$_2$CH$_2$CH$_2$-4-MeO-phenyl,
(Z)-2-HOCH$_2$CH=CH-4-MeO-phenyl,
(E)-2-HOCH$_2$CH=CH-4-MeO-phenyl,
(Z)-2-CH$_3$CO$_2$CH=CH-4-MeO-phenyl,
(E)-2-CH$_3$CO$_2$CH=CH-4-MeO-phenyl,
2-CH$_3$OCH$_2$CH$_2$-4-MeO-phenyl,
2-F-4-MeO-phenyl, 2-Cl-4-F-phenyl, cyclohexyl, cyclopentyl, cyclohexylmethyl,
benzyl, 2-F-benzyl, 3-F-benzyl, 4-F-benzyl,
3-MeO-benzyl, 3-OH-benzyl, 2-MeO-benzyl,
2-OH-benzyl, 2-MeOC(=O)-3-MeO-phenyl,
2-Me-4-CN-phenyl, 2-Me-3-CN-phenyl,
2-Me-4-MeS-phenyl, 2-CF$_3$-4-CN-phenyl,
2-CHO-phenyl, 3-CHO-phenyl, 2-HOCH$_2$-phenyl,
3-HOCH$_2$-phenyl, 3-MeOCH$_2$-phenyl,
3-Me$_2$NCH$_2$-phenyl, 3-CN-4-F-phenyl,
2-Me-4-H$_2$NCO-phenyl, 2-Me-4-MeOC(=O)-phenyl,
3-H$_2$NCO-4-F-phenyl, 2-Me$_2$NCH$_2$-4-MeO-phenyl-,
2-Me-4-CH$_3$C(=O)-phenyl,
phenyl-NH—, (1-naphthyl)-NH—,
(2-naphthyl)-NH—, (2-[1,1'-biphenyl])-NH—,
(3-[1,1'-biphenyl])-NH—, (4-[1,1'-biphenyl])-NH—,
(2-F-phenyl)-NH—, (2-Cl-phenyl)-NH—,
(2-CF$_3$-phenyl)-NH—, (2-CH$_3$-phenyl)-NH—,
(2-OMe-phenyl)-NH—, (2-CN-phenyl)-NH—,
(2-OCF$_3$-phenyl)-NH—, (2-SMe-phenyl)-NH—,
(3-F-phenyl)-NH—, (3-Cl-phenyl)-NH—,
(3-CF$_3$-phenyl)-NH—, (3-CH$_3$-phenyl)-NH—,
(3-OMe-phenyl)-NH—, (3-CN-phenyl)-NH—,
(3-OCF$_3$-phenyl)-NH—, (3-SMe-phenyl)-NH—,
(4-F-phenyl)-NH—, (4-Cl-phenyl)-NH—,
(4-CF$_3$-phenyl)-NH—, (4-CH$_3$-phenyl)-NH—,
(4-OMe-phenyl)-NH—, (4-CN-phenyl)-NH—,
(4-OCF$_3$-phenyl)-NH—, (4-SMe-phenyl)-NH—,
(2,3-diCl-phenyl)-NH—, (2,4-diCl-phenyl)-NH—,
(2,5-diCl-phenyl)-NH—, (2,6-diCl-phenyl)-NH—,
(3,4-diCl-phenyl)-NH—, (3,5-diCl-phenyl)-NH—,
(2,3-diF-phenyl)-NH—, (2,4-diF-phenyl)-NH—,
(2,5-diF-phenyl)-NH—, (2,6-diF-phenyl)-NH—,
(3,4-diF-phenyl)-NH—, (3,5-diF-phenyl)-NH—,
(2,3-diCH$_3$-phenyl)-NH—, (2,4-diCH$_3$-phenyl)-NH—,
(2,5-diCH$_3$-phenyl)-NH—, (2,6-diCH$_3$-phenyl)-NH—,
(3,4-diCH$_3$-phenyl)-NH—, (3,5-diCH$_3$-phenyl)-NH—,
(2,3-diCF$_3$-phenyl)-NH—, (2,4-diCF$_3$-phenyl)-NH—,
(2,5-diCF$_3$-phenyl)-NH—, (2,6-diCF$_3$-phenyl)-NH—,
(3,4-diCF$_3$-phenyl)-NH—, (3,5-diCF$_3$-phenyl)-NH—,
(2,3-diOMe-phenyl)-NH—, (2,4-diOMe-phenyl)-NH—,
(2,5-diOMe-phenyl)-NH—, (2,6-diOMe-phenyl)-NH—,
(3,4-diOMe-phenyl)-NH—, (3,5-diOMe-phenyl)-NH—,
(2-F-3-Cl-phenyl)-NH—, (2-F-4-Cl-phenyl)-NH—,
(2-F-5-Cl-phenyl)-NH—, (2-F-6-Cl-phenyl)-NH—,
(2-F-3-CH$_3$-phenyl)-NH—, (2-F-4-CH$_3$-phenyl)-NH—,
(2-F-5-CH$_3$-phenyl)-NH—, (2-F-6-CH$_3$-phenyl)-NH—,
(2-F-3-CF$_3$-phenyl)-NH—, (2-F-4-CF$_3$-phenyl)-NH—,
(2-F-5-CF$_3$-phenyl)-NH—, (2-F-6-CF$_3$-phenyl)-NH—,
(2-F-3-OMe-phenyl)-NH—, (2-F-4-OMe-phenyl)-NH—,
(2-F-5-OMe-phenyl)-NH—, (2-F-6-OMe-phenyl)-NH—,
(2-Cl-3-F-phenyl)-NH—, (2-Cl-4-F-phenyl)-NH—,
(2-Cl-5-F-phenyl)-NH—, (2-Cl-6-F-phenyl)-NH—,
(2-Cl-3-CH$_3$-phenyl)-NH—, (2-Cl-4-CH$_3$-phenyl)-NH—,
(2-Cl-5-CH$_3$-phenyl)-NH—, (2-Cl-6-CH$_3$-phenyl)-NH—,
(2-Cl-3-CF$_3$-phenyl)-NH—, (2-Cl-4-CF$_3$-phenyl)-NH—,
(2-Cl-5-CF$_3$-phenyl)-NH—, (2-Cl-6-CF$_3$-phenyl)-NH—,
(2-Cl-3-OMe-phenyl)-NH—, (2-Cl-4-OMe-phenyl)-NH—,
(2-Cl-5-OMe-phenyl)-NH—, (2-Cl-6-OMe-phenyl)-NH—,
(2-CH$_3$-3-F-phenyl)-NH—, (2-CH$_3$-4-F-phenyl)-NH—,
(2-CH$_3$-5-F-phenyl)-NH—, (2-CH$_3$-6-F-phenyl)-NH—,
(2-CH$_3$-3-Cl-phenyl)-NH—, (2-CH$_3$-4-Cl-phenyl)-NH—,
(2-CH$_3$-5-Cl-phenyl)-NH—, (2-CH$_3$-6-Cl-phenyl)-NH—,
(2-CH$_3$-3-CF$_3$-phenyl)-NH—, (2-CH$_3$-4-CF$_3$-phenyl)-NH—,
(2-CH$_3$-5-CF$_3$-phenyl)-NH—, (2-CH$_3$-6-CF$_3$-phenyl)-NH—,
(2-CH$_3$-3-OMe-phenyl)-NH—, (2-CH$_3$-4-OMe-phenyl)-NH—,
(2-CH$_3$-5-OMe-phenyl)-NH—, (2-CH$_3$-6-OMe-phenyl)-NH—,
(2-CF$_3$-3-F-phenyl)-NH—, (2-CF$_3$-4-F-phenyl)-NH—,
(2-CF$_3$-5-F-phenyl)-NH—, (2-CF$_3$-6-F-phenyl)-NH—,
(2-CF$_3$-3-Cl-phenyl)-NH—, (2-CF$_3$-4-Cl-phenyl)-NH—,
(2-CF$_3$-5-Cl-phenyl)-NH—, (2-CF$_3$-6-Cl-phenyl)-NH—,
(2-CF$_3$-3-CH$_3$-phenyl)-NH—, (2-CF$_3$-4-CH$_3$-phenyl)-NH—,
(2-CH$_3$-5-CF$_3$-phenyl)-NH—, (2-CF$_3$-6-CH$_3$-phenyl)-NH—,
(2-CF$_3$-3-OMe-phenyl)-NH—, (2-CF$_3$-4-OMe-phenyl)-NH—,
(2-CF$_3$-5-OMe-phenyl)-NH—, (2-CF$_3$-6-Ome-phenyl)-NH—,
(2-OMe-3-F-phenyl)-NH—, (2-OMe-4-F-phenyl)-NH—,
(2-OMe-5-F-phenyl)-NH—, (2-OMe-6-F-phenyl)-NH—,
(2-OMe-3-Cl-phenyl)-NH—, (2-OMe-4-Cl-phenyl)-NH—,
(2-OMe-5-Cl-phenyl)-NH—, (2-OMe-6-Cl-phenyl)-NH—,
(2-OMe-3-CH$_3$-phenyl)-NH—, (2-OMe-4-CH$_3$-phenyl)-NH—,
(2-OMe-5-CH$_3$-phenyl)-NH—, (2-OMe-6-CH$_3$-phenyl)-NH—,
(2-OMe-3-CF$_3$-phenyl)-NH—, (2-OMe-4-CF$_3$-phenyl)-NH—,
(2-OMe-5-CF$_3$-phenyl)-NH—, (2-OMe-6-CF$_3$-phenyl)-NH—
(3-CF$_3$-4-Cl-phenyl)-NH—, (3-CF$_3$-4-C(O)CH$_3$-phenyl)-NH—,
(2,3,5-triCl-phenyl)-NH—, (3-CH$_3$-4-CO$_2$Me-phenyl)-NH—, and
(3-CHO-4-OMe-phenyl)-NH—; and R$^{31}$, at each occurrence, is independently selected from H, —OH, F, Cl, —CF$_3$, —OCF$_3$, methyl, methyl-C(=O)—, methoxy, methylthio, methyl-S(=O)—, and methyl-SO$_2$—.

In a second embodiment, the present invention provides a pharmaceutical composition comprising a compound of Formula (I) and a pharmaceutically acceptable carrier.

In a third embodiment, the present invention provides a method for the treatment a central nervous system disorder comprising administering to a host in need of such treatment a therapeutically effective amount of a compound of Formula (I), or a pharmaceutically acceptable salt thereof, wherein the compound is a 5HT2a antagonist or a 5HT2c agonist.

In a preferred embodiment the compound is a 5HT2a antagonist.

In another preferred embodiment the compound is a 5HT2c agonist.

In a more preferred embodiment the present invention provides a method for the treatment central nervous system disorders including obesity, anxiety, depression, psychosis, schizophrenia, sleep disorders, sexual disorders, migraine, conditions associated with cephalic pain, social phobias, and gastrointestinal disorders such as dysfunction of the gastrointestinal tract motility comprising administering to a host in need of such treatment a therapeutically effective amount of a compound of Formula (I).

In a further preferred embodiment the central nervous system disorder comprises obesity.

In another further preferred embodiment the central nervous system disorder comprises schizophrenia.

In another further preferred embodiment the central nervous system disorder comprises depression.

In another further preferred embodiment the central nervous system disorder comprises anxiety.

In a fourth embodiment the present invention provides novel compounds of Formula (I) or pharmaceutically acceptable salt forms thereof for use in therapy.

In a fifth embodiment the present invention provides the use of novel compounds of Formula (I) or pharmaceutically acceptable salt forms thereof for the manufacture of a medicament for the treatment of central nervous system disorders including obesity, anxiety, depression, psychosis, schizophrenia, sleep disorders, sexual disorders, migraine, conditions associated with cephalic pain, social phobias, and gastrointestinal disorders.

Generally, the compounds of this invention are comprised of a Serotonin receptor specific substituent "$S^{ag}$" and a heterocyclic serotonin receptor ligand Template "$T^{ag}$". The serotonin receptor specific substituent contains an aryl moiety either directly bound to the "$T^{ag}$" or bound through an amine. Applicants have discovered that said serotonin receptor specific substituent imparts unexpected sensitivity and selectivity to the serotonin receptor.

The heterocyclic serotonin receptor ligand template "$T^{ag}$" comprises templates T-1 through T-11 disclosed herein and summarized below.

Template T-1: comprising the structure:

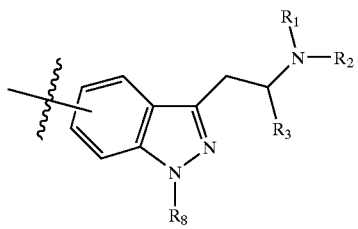

is disclosed in Cerebrus Pharmaceuticals patent application WO 00/12482.

Template T-2: comprising the structure:

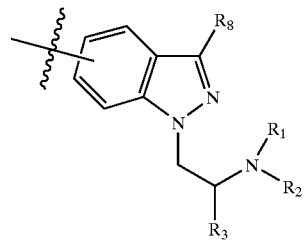

is disclosed in Cerebrus Pharmaceuticals patent application WO 00/12481.

Template T-3: comprising the structure:

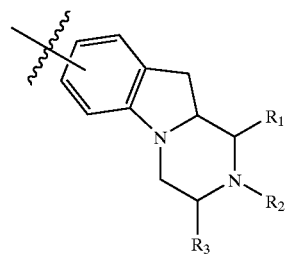

is disclosed in Vernalis Research Limited patent application WO 00/44753.

Template T-4: comprising the structure:

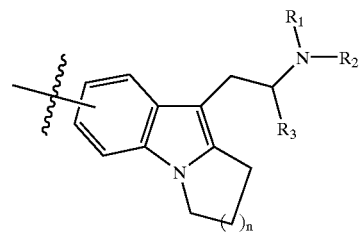

is disclosed in Cerebrus Pharmaceuticals patent application WO 00/12510.

Template T-5: comprising the structure:

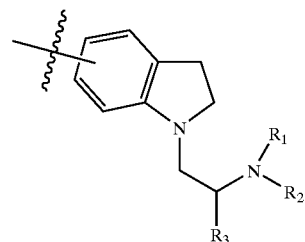

is disclosed in Cerebrus Pharmaceuticals patent application WO 00/12475.

Template T-6: comprising the structure:

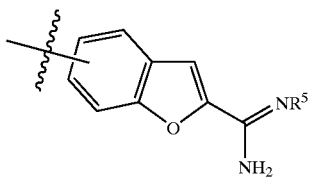

is disclosed in Hoffman-LaRoche AG patent application WO 97/42183.

Template T-7: comprising the structure:

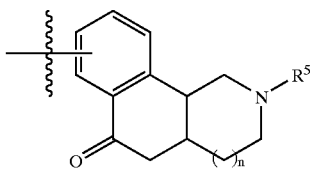

is disclosed in Hoffman-LaRoche AG patent application WO 98/30546.

Template T-8: comprising the structure:

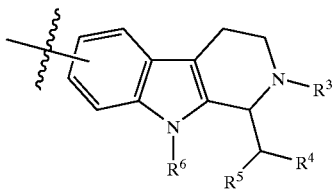

is disclosed in Novo-Nordisk A/S patent application WO 97/00871.

Template T-9: comprising the structure:

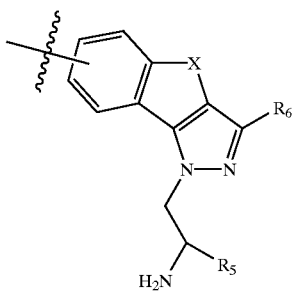

is disclosed in Hoffman-LaRoche AG patent application CA 2,153,937.

Template T-10: comprising the structure:

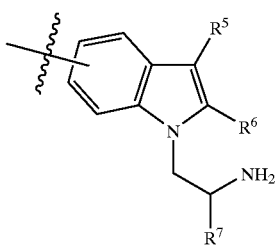

is disclosed in Hoffman-LaRoche AG patent application EP 0655440.

Template T-11: comprising the structure:

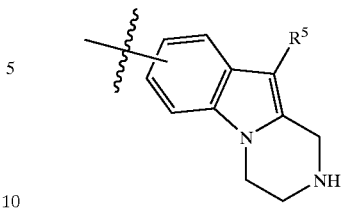

is disclosed in Hoffman-LaRoche AG patent application CA 2,097,465.

The above description of heterocyclic serotonin receptor ligand templates for use in the present invention were taken from published applications: 1) WO 00/12482; 2) WO 00/12481; 3) WO 00/44753; 4) WO 00/12510; 5) WO 00/12475; 6) WO 97/42183; 7) WO 98/30546; 8) WO 97/00871; 9) CA 2,153,937; 10) EP 0655440; and 11) CA 2,097,465; the disclosure of said patent applications for methods of preparing said templates being incorporated herein by reference. Reference should be made to said published applications for their full disclosures on the methods of preparing said templates.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. C is and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced.

When any variable (e.g. $R^{16}$, $R^{33}$, etc.) occurs more than one time in any constituent or formula for a compound, its definition at each occurrence is independent of its definition at every other occurrence. Thus, for example, if a group is shown to be substituted with 0–5 $R^{33}$, then said group may optionally be substituted with up to five $R^{33}$ groups and $R^{33}$ at each occurrence is selected independently from the definition of $R^{33}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms; for example, "$C_1$–$C_6$ alkyl" or "$C_{1-6}$ alkyl" denotes alkyl having 1 to 6 carbon atoms. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

"Alkenyl" or "alkenylene" is intended to include hydrocarbon chains of either a straight or branched configuration having the specified number of carbon atoms, for example "$C_{2-6}$ alkenyl", and one or more unsaturated carbon-carbon bonds which may occur in any stable point along the chain. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either a straight or branched configuration, having the specified number of carbon atoms, for example "$C_{2-6}$ alkynyl", and one or more carbon-carbon triple bonds which may occur in any stable point along the chain, such as ethynyl, propynyl, butynyl, pentynyl, hexynyl and the like.

"Cycloalkyl" is intended to include saturated ring groups, having the specified number of carbon atoms. For example, "$C_3$–$C_6$ cycloalkyl" denotes such as cyclopropyl, cyclobutyl, cyclopentyl, or cyclohexyl.

"Alkoxy" or "alkyloxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Similarly, "alkylthio" is represents an alkyl group as defined above with the indicated number of carbon atoms attached through a sulpher bridge.

"Halo" or "halogen" as used herein refers to fluoro, chloro, bromo, and iodo; and "counterion" is used to represent a small, negatively charged species such as chloride, bromide, hydroxide, acetate, sulfate, and the like.

"Haloalkyl" is intended to include both branched and straight-chain saturated aliphatic hydrocarbon groups having the specified number of carbon atoms, substituted with 1 or more halogen (for example —$C_vF_w$, where v=1 to 3 and w=1 to (2v+1)). Examples of haloalkyl include, but are not limited to, trifluoromethyl, trichloromethyl, pentafluoroethyl, pentachloroethyl, 2,2,2-trifluoroethyl, heptafluoropropyl, and heptachloropropyl.

As used herein, "carbocycle" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic ring" or "heterocyclic ring system" is intended to mean a stable 5- to 7-membered monocyclic or bicyclic or 7- to 14-membered bicyclic heterocyclic ring which is saturated partially unsaturated or unsaturated (aromatic), and which consists of carbon atoms and 1, 2, 3 or 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, imidazolopyridinyl, 1H-indazolyl, indolenyl, indolinyl, indolizinyl, indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolopyridinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thiazolopyridinyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Preferred heterocycles include, but are not limited to, pyridinyl, furanyl, thienyl, pyrrolyl, pyrazolyl, pyrazinyl, piperazinyl, imidazolyl, indolyl, benzimidazolyl, 1H-indazolyl, oxazolidinyl, benzotriazolyl, benzisoxazolyl, benzoxazolyl, oxindolyl, benzoxazolinyl, benzthiazolyl, benzisothiazolyl, isatinoyl, isoxazolopyridinyl, isothiazolopyridinyl, thiazolopyridinyl, oxazolopyridinyl, imidazolopyridinyl, and pyrazolopyridinyl. Preferred 5 to 6 membered heterocycles include, but are not limited to, pyridinyl, furanyl, thienyl, pyrrolyl, pyrazolyl, pyrazinyl, piperazinyl, imidazolyl, and oxazolidinyl. Also included are fused ring and spiro compounds containing, for example, the above heterocycles.

As used herein, the term "bicyclic heterocyclic ring system" is intended to mean a stable 9- to 10-membered bicyclic heterocyclic ring formed from the substituent NR$^{12}$R$^{13}$, which is partially unsaturated or unsaturated (aromatic), and which consists of carbon atoms, a nitrogen atom, and 1 or 2 additional heteroatoms independently selected from the group consisting of N, O and S. The additional nitrogen or sulfur heteroatoms may optionally be oxidized. The heterocyclic ring is attached to its pendant group by the nitrogen atom of the group $NR^{12}R^{13}$ and for which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. The term "bicyclic heterocyclic ring system" is intended to be a subset of the term "heterocyclic ring system". Preferred examples of a 9-to 10-membered bicyclic heterocyclic ring system are benzimidazolyl, benzimidazolinyl, benzoxazolinyl, dihydrobenzthiazolyl, dihydrodioxobenzthiazolyl, benzisoxazolinyl, 1H-indazolyl, indolyl, indolinyl, isoindolinyl, tetrahydro-isoquinolinyl, tetrahydro-quinolinyl, and benzotriazolyl.

As used herein, the term "aryl", or aromatic residue, is intended to mean an aromatic moiety containing six to ten carbon atoms, such as phenyl, pyridinyl and naphthyl.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

"Prodrugs" are intended to include any covalently bonded carriers which release the active parent drug according to formula (I) in vivo when such prodrug is administered to a mammalian subject. Prodrugs of a compound of formula (I) are prepared by modifying functional groups present in the compound in such a way that the modifications are cleaved, either in routine manipulation or in vivo, to the parent compound. Prodrugs include compounds of formula (I) wherein a hydroxy, amino, or sulfhydryl group is bonded to any group that, when the prodrug or compound of formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of Formula (I), and the like. "Stable compound" and "stable structure" are meant to indicate a compound that is sufficiently robust to survive isolation to a useful degree of purity from a reaction mixture, and formulation into an efficacious therapeutic agent.

Synthesis

Throughout the details of the invention, the following abbreviations are used with the following meanings:

| Reagents: | |
| --- | --- |
| MCPBA | m-chloroperoxybenzoic acid |
| DIBAL | diisobutyl aluminum hydride |
| $Et_3N$ | triethylamine |
| TFA | trifluoroacetic acid |
| LAH | lithium aluminum hydride |
| NBS | N-bromo succinimide |
| Red-Al | Sodium bis (2-methoxyethoxy) aluminum hydride |
| $Pd_2dba_3$ | Tris (dibenzylideneacetone) dipalladium (0) |
| ACE-Cl | 2-chloroethylchloroformate |

| Solvents: | |
| --- | --- |
| THF | tetrahydrofuran |
| MeOH | methanol |
| EtOH | ethanol |
| EtOAc | ethyl acetate |
| HOAc | acetic acid |
| DMF | dimethyl formamide |
| DMSO | dimethyl sulfoxide |
| DME | dimethoxyethane |
| $Et_2O$ | diethylether |
| iPrOH | isopropanol |

| Others: | |
| --- | --- |
| Ar | aryl |
| Ph | phenyl |
| Me | methyl |
| Et | ethyl |
| BOC | tert-butoxycarbonyl |
| CBZ | benzyloxycarbonyl |
| Bn | benzyl |
| Bu | butyl |
| Pr | propyl |
| cat. | catalytic |
| rt | room temperature |

The preparation of compounds of Formula (I) of the present invention may be carried out in a convergent or sequential synthetic manner. Detailed synthetic preparations of the compounds of Formula (I) are shown in the following reaction schemes. The skills required in preparation and purification of the compounds of Formula (I) and the intermediates leading to these compounds are known to those skilled in the art. Purification procedures include, but are not limited to, normal or reverse phase chromatography, crystallization, and distillation.

Preferred methods for the preparation of the compounds of the present invention include, but are not limited to, those shown in the schemes below. The substitutions are as described and defined in the claims. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

This invention details the preparation of compounds where X=aryl and heteroaryl groups chosen from group 1 below and defined in the claims of this invention. The Y component of these derivatives is chosen from the previously identified serotonin receptor ligands in Table 1. The diversity of the chosen Y components of each of these derivatives has been defined and is incorporated into these derivatives by the references.

One example of the preparation of these various aryl substituted serotonin ligands is shown in Scheme 1. The core system is shown as a representation of the ligands from Table 1. Starting with a halogen substituted ligand from the list of Table 1 the elaboration to an aryl substituted derivative is straightforward. Those skilled in the art will recognize the utility of aryl bromides of type (III) in allowing for the coupling of this moiety with an arylboronic acid (IV) to afford biaryl derivatives of type (V). This transformation, commonly known as a Suzuki coupling is utilized to afford many types of functionalized derivatives. For a review and leading references of palladium catalyzed cross coupling reactions, see Miyaura, N., Suzuki, A., *Chem. Rev.*, 1995, 2457. One such procedure entails treatment of the aryl bromide (III) with a functionalized aryl boronic acid in the presence of a catalytic Pd(0) species, such as Pd(PPh$_3$)$_4$, Pd(PPh$_3$)$_2$Cl$_2$, Pd(OAc)$_2$, Pd$_2$(dba)$_3$ and a suitable ligand such as PPh$_3$, AsPh$_3$, etc., or other such Pd(0) catalyst, and a base such as Na$_2$CO$_3$ or Et$_3$N in a suitable solvent such as DMF, toluene, THF, DME or the like, to afford the coupled derivative (V).

SCHEME 1

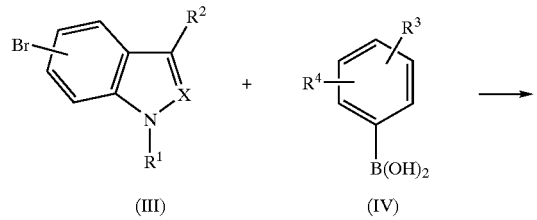

(III)    (IV)

-continued

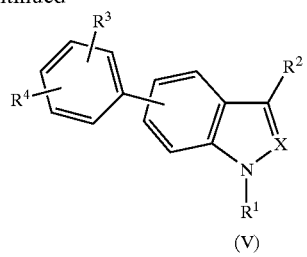

(V)

In addition, formation of the aryl boronate ester (VI) from the bromine derivative (III) (i.e. (I, R$^7$=B(OH)$_2$)) would allow for greater diversity in the subsequent coupling of this aryl boronate with commercially available haloaromatic derivatives in a similar Suzuki coupling strategy as described above to afford the derivatives of type (I), shown in Scheme 2. This transformation can be effected, for example, by treatment of the arylbromide (III) with pinacol diboron and a base such as potassium acetate, in the presence of a Pd(0) catalyst, such as tetrakis (triphenylphosphine) palladium (0), in DMF at 80° C. to afford the boronate ester (VI). Subsequent Pd(0) catalyzed coupling of this boronate ester (VI) with an arylbromide (VII) under basic conditions affords the Suzuki coupled adduct (V).

SCHEME 2

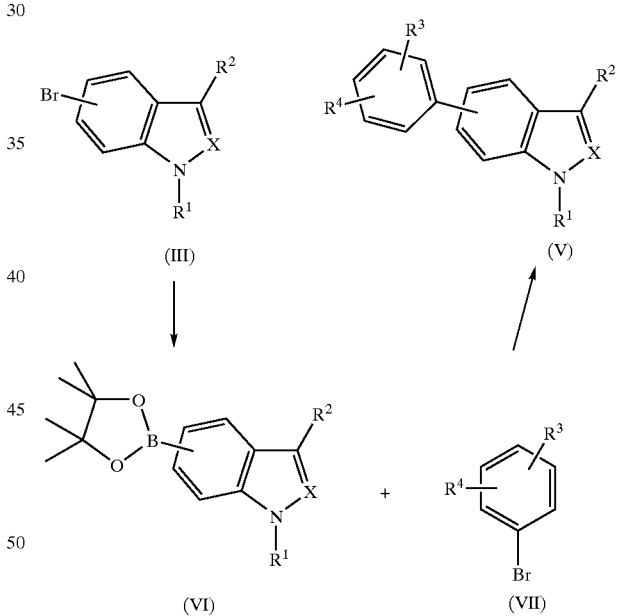

Preparation of nitrogen linked biaryl derivatives is described in Scheme 3. Treatment of arylbromide derivatives of type (III) with diphenylmethylimine under Pd$_2$(dba)$_3$, BINAP catalyzed conditions followed by basic hydrolysis (NH$_2$OH—HCl, NaOAc, MeOH) of the imine affords the primary aniline derivative (VIII). Coupling of these anilines with various arylbromides (IV) under Pd(0) catalyzed conditions affords the amine linked biaryl derivatives of type (IX) (see A. S. Guram, R. A. Rennels and S. L. Buchwald, *Angew. Chem. Int. Ed. Engl.*, 1995,34,1348). These amine derivatives can also be alkylated to afford the tertiary anilines (X) by standard procedures known to those in the art. Leading references to these as well as related transformations may be found in Larock, R. C., *Comprehensive Organic Transformations*, VCH Publishers, New York, 1989.

SCHEME 3

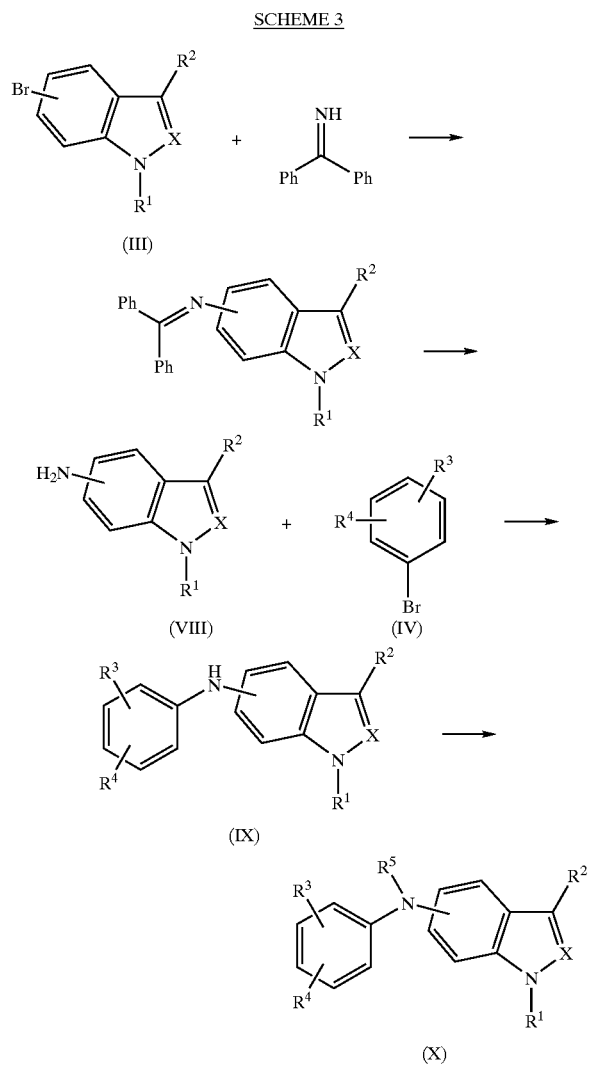

Initiating the synthesis in the above Schemes with derivatives of type (III) with a nitro group on the aromatic ring is an alternate approach to these coupling procedures. Use of an arylnitro group to effect this coupling either directly via the diazonium salt derivative or indirectly through transformation of the diazonium salt to an aryl bromide via Sandoz reaction conditions (see Larock, R. C., *Comprehensive Organic Transformations*, VCH Publishers, New York, 1989) expands the utility of this approach. More highly substituted nitrobenzenes starting materials can be obtained by traditional synthetic manipulation (i.e aromatic substitution) and are known by those in the art. As was the case with the boronic acid approach, the ability to couple the aryl bromide of derivatives of type (III) with an aniline affords greater breadth to this approach.

Additionally, use of an arylstannane to effect this substitution is shown in Scheme 4. Treatment of the aryl bromide (III) with hexabutyldistannane and cat. Pd(OAc)$_2$ and triphenylphosphine affords the arylstannane (XI). The utility of an arylstannane in performing couplings with arylbromides has been well documented in the literature (see J. K. Stille, *Angew. Chem. Int. Ed. Engl.*, 1986,25,508, and T. N. Mitchell, *Synthesis*, 1992,803.). Thus, treatment of the arylstannane (XI) with an arylbromide (IV) under Pd(0) catalyzed conditions affords biaryl coupled derivatives of type (V).

SCHEME 4

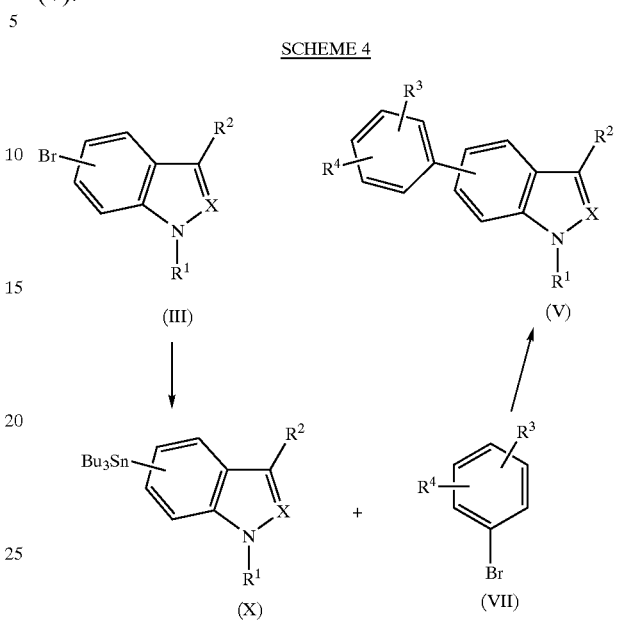

In the case of racemic deivatives of type (I), the corresponding enantiomers can be isolated by separation of the racemic mixture on a chiral stationary phase column utilizing normal or reverse phase HPLC techniques. Alternatively, a diastereomeric mixture of (I) can be prepared by treatment of a basic derivative with an appropriate chiral acid (or suitably activated derivative), for example dibenzoyl tartrate or the like (see, for example, Kinbara, K., et. al., *J. Chem. Soc., Perkin Trans.* 2, 1996, 2615; and Tomori, H., et. al., *Bull. Chem. Soc. Jpn.*, 1996, 3581). The diastereomers would then be separated by traditional techniques (i.e. silica chromatography, crystallization, HPLC, etc) followed by removal of the chiral auxiliary to afford enantiomerically pure (I).

In the cases where a nitrogen has been protected in the course of the synthesis (i.e. $R^1$=Boc, Bn, CBZ, $CO_2R$), it may be removed under a variety of conditions as described in Greene, T. W., Wuts, P. G. W., "Protective Groups in Organic Synthesis, 2nd Edition", John Wiley and Sons, Inc., New York, pages 309–405, 1991.

Utility

The compounds of the present invention are expected to have therapeutic utility for illnesses or disorders involving the neurotransmitter serotonin (5-hydroxy tryptamine or 5-HT) and either agonism or antagonism of 5-HT2 receptors, which can be demonstrated by the assays described below. Therapeutic utility for these illnesses or disorders could involve numerous biological processes affected by serotonin including, but not limited to, appetite, mood, sleep, sexual activity, and arterial constriction. These biological processes may also be important to numerous central nervous system (CNS) disorders including those related to the affective disorders of depression, anxiety, psychosis, and schizophrenia, as well as, disorders of food intake such as anorexia, bulemia, and obesity. The compounds of the present invention potentially have therapeutic utility in other conditions in which serotonin has been implicated, such as migraine, attention deficit disorder or attention deficit hyperactivity disorder, addictive behavior, and obsessive-compulsive disorder, as well as, conditions associated with cephalic pain, social phobias, and gastrointestinal disorders such as dysfunction of the gastrointestinal tract motility. Lastly, compounds of the present invention potentially have therapeutic utility in neurodegenerative diseases and traumatic conditions represented by the examples of Alzheimer's disease and brain/spinal cord trauma.

The pharmacological analysis of each compound for either antogonism or agonism of at 5-HT2A and 5-HT2C receptors consists of in vitro and in vivo studies. In vitro analyses includs $K_i$ determinations at 5-HT2A and 5-HT2C receptors and an assessment of functional (i.e., agonism or antagonism) activity at each receptor class by IP3 hydrolysis assays. Additional receptor assays can be conducted to evaluate receptor specificity of 5-HT2A and 5-HT2C receptors over monoamine and nuisance receptors (e.g. histamine, dopamine, and muscarinic). A compound is considered active as a 5-HT2A antagonist or a 5-HT2C agonist if it has an $IC_{50}$ value or a $K_i$ value of less than about 50 micromolar; preferably less than about 0.1 micromolar; more preferably less than about 0.01 micromolar. Using the assays disclosed herein, compounds of the present invention are expected to have an $IC_{50}$ value of less than about 50 micromolar for 5-HT2A antagonism or 5-HT2C agonism.

In vivo assays assess compound activity in a variety of behavioral paradigms including quipazine head twitch, acute and chronic feeding models, anxiety and depression models (learned-helplessness, elevated plus maze, Geller-Siefter, conditioned taste aversion, taste reactivity, satiety sequence). In aggregate, these models can reflect activity as a 5-HT2A antagonist (quipazine head twitch, depression models) or 5-HT2C agonist (feeding models, anxiety models, depression models) and provide some indication as to bioavailability, metabolism and pharmacokinetics.

Radioligand binding experiments can be conducted on recombinant human 5-HT2A and 5-HT2C receptors expressed in HEK293E cells. The affinities of compounds of the present invention to bind at these receptors can be determined by their capacity to compete for [$^{125}$I]-1-(2,5-dimethoxy-4-iodophenyl)-2-amino-propane (DOI) binding at the 5-HT2A or 5-HT2C. General references for binding assays include 1) Lucaites V L, Nelson D L, Wainscott D B, Baez M (1996) Receptor subtype and density determine the coupling repertoire of the 5-HT2 receptor subfamily. Life Sci., 59(13):1081–95. J Med Chem Jan. 31, 1988 (1):5–7; 2) Glennon R A, Seggel M R, Soine W H, Herrick-Davis K, Lyon R A, Titeler M (1988) [125I]-1-(2,5-dimethoxy-4-iodophenyl)-2-amino-propane: an iodinated radioligand that specifically labels the agonist high-affinity state of 5-HT2 serotonin receptors. J Med. Chem. 31(1):5–7 and 3) Leonhardt S, Gorospe E, Hoffman B J, Teitler M (1992) Molecular pharmacological differences in the interaction of serotonin with 5-hydroxytryptamine1C and 5-hydroxytryptamine2 receptors. Mol Pharmacol., 42(2):328–35.

The functional properties of compounds (efficacy and potency) can be determined in whole cells expressing 5-HT2A or 5-HT2C receptors by assessing their ability to stimulate or inhibit receptor-mediated phosphoinositol hydrolysis. The procedures generally practiced by one skilled in the art are described below.

In vitro Binding Assays

Stable Expression of 5-HT2A and 5-HT2C Receptors in HEK293E Cells.

Stable cell lines were generated by transfecting 293EBNA cells with plasmids containing human 5-HT2A, 5-HT2B, or 5-HT2C (VNV edited isoform) cDNA using calcium phosphate. These plasmids also contained the cytomegalovirus (CMV) immediate early promoter to drive receptor expression and EBV oriP for their maintenance as an extrachromosomal element, and the hph gene from E. Coli to yield hygromycin B resistance (Horlick et al., 1997). Transfected cells were maintained in Dulbecco's Modified Eagle medium (DMEM) containing dialyzed 10% fetal bovine serum at 37° C. in a humid environment (5% $CO_2$) for 10 days. The 5-HT2A cells were adapted to spinner culture for bulk processing whereas it was necessary to maintain the other lines as adherent cultures. On the day of harvest, cells were washed in phosphate-buffered saline (PBS), counted, and stored at –80° C.

Membrane Preparation

On the day of assay, pellets of whole cells (containing approximately 1×108 cells) expressing the 5-HT2A or 5-HT2C receptor were thawed on ice and homogenized in 50 mM Tris HCl (pH 7.7) containing 1.0 mM EDTA using a Brinkman Polytron (PT-10, setting 6 for 10 sec). The homogenate was centrifuged at 48,000×g for 10 min and the resulting pellet washed twice by repeated homogenization and centrifugation steps. The final pellet was resuspended in tissue buffer and protein determinations were made by the bichichoninic acid (BCA) assay (Pierce Co., IL) using bovine serum albumin as the standard.

Radioligand Binding Assays for the 5-HT2A and 5-HT2C Receptors.

Radioligand binding studies were conducted to determine the binding affinities (KI values) of compounds for the human recombinant 5-HT2A, 5-HT2B, and 5-HT2C receptors (Fitzgerald et al., 1999). Assays were conducted in disposable polypropylene 96-well plates (Costar Corp., Cambridge, Mass.) and were initiated by the addition of 5-HT2A 5-HT2B, or 5-HT2C membrane homogenate in tissue buffer (10–30 (g/well) to assay buffer (50 mM Tris HCl, 0.5 mM EDTA, 10 mM pargyline, 10 mM $MgSO_4$, 0.05% ascorbic acid, pH 7.5) containing [$^{125}$I]DOI for the 5-HT2A and 5-HT2C receptors (0.3–0.5 nM, final) or [$^3$H] LSD (2–2.5 nM, final) for the 5-HT2B receptor, with or without competing drug (i.e, newly synthesized chemical entity). For a typical competition experiment, a fixed concentration of radioligand was competed with duplicate concentrations of ligand (12 concentrations ranging from 10 picomolar to 10 micromolar). The reaction mixtures were incubated to equilibrium for 45 min at 37° C. and terminated by rapid filtration (cell harvestor; Inotech Biosystems Inc., Lansing, Mich.) over GFF glass-fiber filters that had been pre-soaked in 0.3% polyethyleneimine. Filters were washed in ice-cold 50 mM Tris HCl buffer (pH 7.5) and then counted in a gamma counter for the 5-HT2A and 5-HT2C assays, or by liquid scintillation spectroscopy for the 5-HT2B assay.

Phosphoinositide Hydrolysis Studies.

The ability of newly synthesized compounds to stimulate phosphoinositide (PI) hydrolysis was monitored in whole cells using a variant (Egan et al., 1998) of a protocol described previously (Berridge et al., 1982). HEK293E cells expressing the human 5-HT2A, 5-HT2B, or 5-HT2C receptor were lifted with 0.5 mM EDTA and plated at a density of 100,000/well onto poly-D-lysine-coated 24-well plates (Biocoat; Becton Dickinson, Bedford, Mass.) in Dulbecco's modified Eagle's serum (DMEM; Gibco BRL) containing high glucose, 2 mM glutamine, 10% dialyzed fetal calf serum, 250 (g/ml hygromycin B, and 250(g/ml G418. Following a 24–48 hr period, the growth media was removed and replaced with DMEM without fetal calf serum and inositol (Gibco BRL). The cells were then incubated with DMEM (without serum and inositol) containing a final concentration of 0.5 uCi/well myo-[$^3$H]inositol for 16–18 hr. Following this incubation, the cells were washed with DMEM (without serum or inositol) containing 10 mM LiCl and 10 (M pargyline and then incubated for 30 min with the same media but now containing one of several test compounds. Reactions were terminated by aspirating the media and lysing the cells by freeze-thaw. [$^3$H]phosphoinositides were extracted with chloroform/methanol (1:2 v/v), separated by anion exchange chromatography (Bio-Rad AG1-X8 resin), and counted by liquid scintillation spectroscopy as described previously (Egan et al., 1998).

Data Analyses

The equilibrium apparent dissociation constants (Ki's) from the competition experiments were calculated using an iterative nonlinear regression curve-fitting program (GraphPad Prism; San Diego, Calif.). For the PI hydrolysis experiments, EC50's were calculated using a one-site 'pseudo' Hill model: $y=((Rmax-Rmin)/(1+R/EC50)_{n}H))+Rmax$ where R=response (DeltaGraph, Monterey, Calif.). Emax (maximal response) was derived from the fitted curve maxima (net IP stimulation) for each compound. Intrinsic activity (IA) was determined by expressing the Emax of a compound as a percentage of the Emax of 5-HT (IA=1.0).

In vivo Experiments for Serotonergic Ligands.

Preclinical Efficacy, Potency, and Side Effect Liability.

a) Anti-Serotonin Efficacy.

Antagonism of Quipazine-Induced Head Twitch in Rat. Quipazine, an agonist at 5-HT receptors, produces a characteristic head twitch response in rats. 5-HT receptor antagonists effectively antagonize this 5-HT agonist-induced behavioral effect (Lucki et al., 1984). Accordingly, the quipazine-induced head twitch model in rat can function as an in vivo behavioral correlate to 5-HT receptor binding. Compounds are administered 30 minutes before behavioral testing (and 25 minutes before quipazine), and a dose-related antagonism of the quipazine response is determined.

b) Antipsychotic Efficacy.

Inhibition of the Conditioned Avoidance Response (CAR) in Rat. Rats are trained to consistently avoid (by climbing onto a pole suspended from the ceiling of the test chamber) an electric foot shock (0.75 mA) delivered to the grid floor of the testing chamber. All antipsychotic drugs effectively inhibit this conditioned avoidance response (Arnt, 1982). The ability of a compound to inhibit this response is used to determine the antipsychotic efficacy of potential drug candidates.

c) Extrapyramidal Side Effect Liability.

Induction of Catalepsy in Rat. Typical antipsychotic drugs produce extrapyramidal side effects (EPS) at clinically effective doses. The most widely accepted preclinical indicator of EPS liability in humans is a drug-induced catalepsy syndrome in rat (Costall and Naylor, 1975), a condition whereby the animal will remain immobile in an externally imposed posture (analogous to a catatonic stupor in humans). Rats are tested for induction of catalepsy in a dose-response test after oral administration of compounds.

d) CNS Penetration; in vivo Brain Receptor Occupancy.

In Vivo Binding. To determine the level of in vivo receptor occupancy, an in vivo receptor binding protocol is used. This procedure uses an appropriate radioligand to label the receptor of interest. For example, to measure both Dopamine D2 and 5-HT2A receptors in vivo, one can use $^3$H—N-methyl spiperone ($^3$H-NMSP), (Frost, et. al. 1987) The procedure uses rats (or mice) fasted overnight. To measure the effects of compounds on the receptors of interest, compounds are dosed, usually p.o. for example in 2 microliters/gram body weight in 0.25% Methocel suspension. The radiolabeled compound (in this example, $^3$H-NMSP) is administered by i.v. tail vein injection (10 microcuries label/200 gram rat). Time course experiments are used to determine the optimal time of binding for both the radiolabeled and unlabeled compound. These optimal time frames are used for all subsequent dose-response experiments. After the appropriate time frame of compound/radioligand exposure, the animals are sacrificed and the relevant brain regions dissected (frontal cortex for 5-HT2A and striatum for D2 receptors) and examined for their content of radioactivity. The level of non-specific binding is determined by examining a brain region known not to contain the receptor of interest (in this case the cerebellum) or by administering an excess of compound known pharmacologically to interact with the receptor.

References

Arnt, J. Acta Pharmacol. et Toxicol. 1982: 51, 321–329.

Berridge M. J., Downes P. C., Hanley M. R. (1982) Lithium amplifies agonist-dependent phosphotidyinositol response in brain and salivary glands. Biochem. J., 206, 587–595.

Costall, B and Naylor, R J. Psychopharmacology. 1975: 43, 69–74.

Egan C. T., Herrick-Davis K., Miller K., Glennon R. A., and Teitler M. (1998) Agonist activity of LSD and lisuride at cloned 5-HT2A and 5-HT2C receptors. Psychopharmacology, 136, 409–414.

Fitzgerald L W, Conklin D S, Krause C M, Marshall A P, Patterson J P, Tran D P, Iyer G, Kostich W A, Largent B L, Hartig P R (1999) High-affinity agonist binding correlates with efficacy (intrinsic activity) at the human serotonin 5-HT2A and 5-HT2C receptors: evidence favoring the ternary complex and two-state models of agonist action. J. Neurochem., 72, 2127–2134.

Frost, J. J., Smith, A. C., Kuhar, M. J., Dannals, R. F., Wagner, H. N., 1987, In Vivo Binding of 3H—N-Methylspiperone to Dopamine and Serotonin Receptors. Life Sciences, 40:987-995.

Horlick, R. A., Sperle, K., Breth, L. A., Reid, C. C., Shen, E. S., Robbinds, A. K., Cooke, G. M., Largent, B. L. (1997) Rapid Generation of stable cell lines expressing corticotrophin-releasing hormone receptor for drug discovery. Protein Expr. Purif. 9, 301–308.

Lucki, I, Nobler, M. S., Frazer, A., 1984, Differential actions of serotonin antagonists on two behavioral models of serotonin receptor activation in the rat. J. Pharmacol. Exp. Ther. 228(1):133–139.

Dosage and Formulation

The serotonin agonist and serotonin antagonist compounds of this invention can be administered as treatment for the control or prevention of central nervous system disorders including obesity, anxiety, depression, psychosis, schizophrenia, sleep and sexual disorders, migraine and other conditions associated with cephalic pain, social phobias, and gastrointestinal disorders such as dysfunction of the gastrointestinal tract motility by any means that produces contact of the active agent with the agent's site of action, i.e., 5-HT2 receptors, in the body of a mammal. It can be administered by any conventional means available for use in conjunction with pharmaceuticals, either as an individual therapeutic agent or in a combination of therapeutic agents. It can be administered alone, but preferably is administered with a pharmaceutical carrier selected on the basis of the chosen route of administration and standard pharmaceutical practice.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. By way of general guidance, a daily dosage of active ingredient can be expected to be about 0.001 to about 1000 milligrams per kilogram of body weight, with the preferred dose being about 0.01 to about 100 mg/kg; with the more preferred dose being about 0.1 to about 30 mg/kg. Advantageously, compounds of the present invention may be administered in a single daily dose, or the total daily dosage may be administered in divided doses of two, three, or four times daily.

Dosage forms of compositions suitable for administration contain from about 1 mg to about 100 mg of active ingredient per unit. In these pharmaceutical compositions the active ingredient will ordinarily be present in an amount of about 0.5–95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. Suitable pharmaceutical carriers are described in *Remington's Pharmaceutical Sciences*, supra, a standard reference text in this field.

Useful pharmaceutical dosage-forms for administration of the compounds of this invention can be illustrated as follows:

Capsules

A large number of unit capsules can be prepared by filling standard two-piece hard gelatin capsules each with 100 mg of powdered active ingredient, 150 mg of lactose, 50 mg of cellulose, and 6 mg magnesium stearic.

Soft Gelatin Capsules

A mixture of active ingredient in a digestible oil such as soybean oil, cottonseed oil or olive oil can be prepared and injected by means of a positive displacement pump into gelatin to form soft gelatin capsules containing 100 mg of the active ingredient. The capsules should then be washed and dried.

Tablets

A large number of tablets can be prepared by conventional procedures so that the dosage unit is 100 mg of active ingredient, 0.2 mg of colloidal silicon dioxide, 5 milligrams of magnesium stearate, 275 mg of microcrystalline cellulose, 11 mg of starch and 98.8 mg of lactose. Appropriate coatings may be applied to increase palatability or delay absorption.

Suspension

An aqueous suspension can be prepared for oral administration so that each 5 mL contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection can be prepared by stirring 1.5% by weight of active ingredient in 10% by volume propylene glycol and water. The solution is sterilized by commonly used techniques.

What is claimed is:

1. A compound of formula (I):

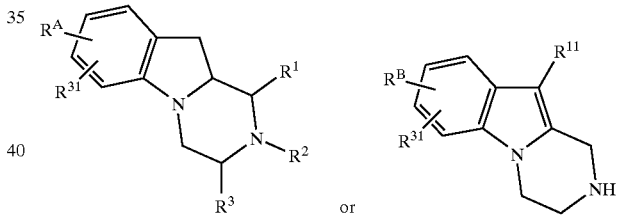

wherein:

$R^A$ is —$NR^{12}R^{13}$;

$R^B$ is —$NR^{12}R^{13}$ or aryl substituted with 0–5 $R^{33}$; and aryl is phenyl, pyridyl, or naphthyl;

$R^1$ is H or $C_{1-4}$ alkyl;

$R^2$ is H or $C_{1-4}$ alkyl;

$R^3$ is H or $C_{1-4}$ alkyl;

$R^{11}$ is H, $C_{1-6}$ alkoxy or $C_{1-6}$ alkyl-S—;

$R^{12}$ is aryl substituted with 0–5 $R^{33}$;

$R^{13}$ is selected from H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —$N(R^{14})$—;

alternatively, $R^{12}$ and $R^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;

$R^{14}$ is H or $C_{1-4}$ alkyl;

$R^{16}$, at each occurrence, is independently selected from
H, OH, halo, CN, NO$_2$, CF$_3$, SO$_2$R$^{45}$, NR$^{46}$R$^{47}$,
—C(=O)H,
C$_{1-4}$ alkyl, C$_{2-4}$ alkenyl, C$_{2-4}$ alkynyl, C$_{1-4}$ haloalkyl,
C$_{1-3}$ haloalkyl-oxy-, and C$_{1-3}$ alkyloxy-;

$R^{31}$, at each occurrence, is independently selected from
H, —OH, halo, —CN, —NO$_2$, —CF$_3$, —OCF$_3$, C$_{1-6}$ alkyl,
C$_{1-4}$ alkyl-C(=O)—, C$_{1-4}$ alkyloxy-, C$_{1-4}$ alkylthio-,
C$_{1-4}$ alkyl-S(=O)—, and C$_{1-4}$ alkyl-SO$_2$—;

$R^{33}$, at each occurrence, is independently selected from
H, OH, halo, CN, NO$_2$, CF$_3$, SO$_2$R$^{45}$, NR$^{46}$R$^{47}$,
—C(=O)H, phenyl, C$_{1-6}$ alkyl, C$_{2-6}$ alkenyl, C$_{2-6}$ alkynyl,
C$_{3-6}$ cycloalkyl, C$_{1-4}$ haloalkyl, C$_{1-4}$ haloalkyl-oxy-,
C$_{1-4}$ alkyloxy-, C$_{1-4}$ alkylthio-, C$_{1-4}$ alkyl-C(=O)—,
C$_{1-4}$ alkyl-C(=O)NH—, C$_{1-4}$ alkyl-OC(=O)—,
C$_{1-4}$ alkyl-C(=O)O—, C$_{3-6}$ cycloalkyl-oxy-,
C$_{3-6}$ cycloalkylmethyl-oxy-;
C$_{1-6}$ alkyl substituted with OH, methoxy, ethoxy, propoxy, butoxy, —SO$_2$R$^{45}$, —NR$^{46}$R$^{47}$, NR$^{46}$R$^{47}$C(=O)—, or (C$_{1-4}$ alkyl)CO$_2$—; and
C$_{2-6}$ alkenyl substituted with OH, methoxy, ethoxy, propoxy, butoxy, —SO$_2$R$^{45}$, —NR$^{46}$R$^{47}$, NR$^{46}$R$^{47}$C(=O)—, or (C$_{1-4}$ alkyl)CO$_2$—;

$R^{45}$ is C$_{1-4}$ alkyl;

$R^{46}$, at each occurrence, is independently selected from H and C$_{1-4}$ alkyl; and $R^{47}$, at each occurrence, is independently selected from H, C$_{1-4}$ alkyl, —C(=O)NH(C$_{1-4}$ alkyl), —SO$_2$(C$_{1-4}$ alkyl),
—C(=O)O(C$_{1-4}$ alkyl), —C(=O)(C$_{1-4}$ alkyl), and —C(=O)H.

2. A compound of claim 1 of formula (I), wherein:
$R^A$ is —NR$^{12}$R$^{13}$;
$R^B$ is —NR$^{12}$R$^{13}$;
phenyl- substituted with 0–5 fluoro;
naphthyl- substituted with 0–3 R$^{33}$;
2-(H$_3$CCH$_2$C(=O))-phenyl- substituted with R$^{33}$;
2-(H$_3$CC(=O))-phenyl- substituted with R$^{33}$;
2-(HC(=O))-phenyl- substituted with R$^{33}$;
2-(H$_3$CCH(OH))-phenyl- substituted with R$^{33}$;
2-(H$_3$CCH$_2$CH(OH))-phenyl- substituted with R$^{33}$;
2-(HOCH$_2$)-phenyl- substituted with R$^{33}$;
2-(HOCH$_2$CH$_2$)-phenyl- substituted with R$^{33}$;
2-(H$_3$COCH$_2$)-phenyl- substituted with R$^{33}$;
2-(H$_3$COCH$_2$CH$_2$)-phenyl- substituted with R$^{33}$;
2-(H$_3$CCH(OMe))-phenyl- substituted with R$^{33}$;
2-(H$_3$COC(=O))-phenyl- substituted with R$^{33}$;
2-(HOCH$_2$CH=CH)-phenyl- substituted with R$^{33}$;
2-((MeOC=O)CH=CH)-phenyl- substituted with R$^{33}$;
2-(methyl)-phenyl- substituted with R$^{33}$;
2-(ethyl)-phenyl- substituted with R$^{33}$;
2-((i-propyl)-phenyl- substituted with R$^{33}$;
2-(F$_3$C)-phenyl- substituted with R$^{33}$;
2-(NC)-phenyl- substituted with R$^{33}$;
2-(H$_3$CO)-phenyl- substituted with R$^{33}$;
2-(fluoro)-phenyl- substituted with R$^{33}$;
2-(chloro)-phenyl- substituted with R$^{33}$;
3-(NC)-phenyl- substituted with R$^{33}$;
3-(H$_3$CO)-phenyl- substituted with R$^{33}$;
3-(fluoro)-phenyl- substituted with R$^{33}$;
3-(chloro)-phenyl- substituted with R$^{33}$;
4-(NC)-phenyl- substituted with R$^{33}$;
4-(fluoro)-phenyl- substituted with R$^{33}$;
4-(chloro)-phenyl- substituted with R$^{33}$;
4-(H$_3$CS)-phenyl- substituted with R$^{33}$;
4-(H$_3$CO)-phenyl- substituted with R$^{33}$;
4-(ethoxy)-phenyl- substituted with R$^{33}$;
4-(i-propoxy)-phenyl- substituted with R$^{33}$;
4-(i-butoxy)-phenyl- substituted with R$^{33}$;
4-(H$_3$CCH$_2$CH$_2$C(=O))-phenyl- substituted with R$^{33}$;
4-((H$_3$C)$_2$CHC(=O))-phenyl- substituted with R$^{33}$;
4-(H$_3$CCH$_2$C(=O))-phenyl- substituted with R$^{33}$;
4-(H$_3$CC(=O))-phenyl- substituted with R$^{33}$;
4-(H$_3$CCH$_2$CH$_2$CH(OH))-phenyl- substituted with R$^{33}$;
4-((H$_3$C)$_2$CHCH(OH))-phenyl- substituted with R$^{33}$;
4-(H$_3$CCH$_2$CH(OH))-phenyl- substituted with R$^{33}$;
4-(H$_3$CCH(OH))-phenyl- substituted with R$^{33}$;
4-(cyclopropyloxy)-phenyl- substituted with R$^{33}$;
4-(cyclobutyloxy)-phenyl- substituted with R$^{33}$; or
4-(cyclopentyloxy)-phenyl- substituted with R$^{33}$;

$R^{12}$ is selected from
phenyl- substituted with 0–5 fluoro;
naphthyl- substituted with 0–3 R$^{33}$;
2-(H$_3$CCH$_2$C(=O))-phenyl- substituted with R$^{33}$;
2-(H$_3$CC(=O))-phenyl- substituted with R$^{33}$;
2-(HC(=O))-phenyl- substituted with R$^{33}$;
2-(H$_3$CCH(OH))-phenyl- substituted with R$^{33}$;
2-(H$_3$CCH$_2$CH(OH))-phenyl- substituted with R$^{33}$;
2-(HOCH$_2$)-phenyl- substituted with R$^{33}$;
2-(HOCH$_2$CH$_2$)-phenyl- substituted with R$^{33}$;
2-(H$_3$COCH$_2$)-phenyl- substituted with R$^{33}$;
2-(H$_3$COCH$_2$CH$_2$)-phenyl- substituted with R$^{33}$;
2-(H$_3$CCH(OMe))-phenyl- substituted with R$^{33}$;
2-(H$_3$COC(=O))-phenyl- substituted with R$^{33}$;
2-(HOCH$_2$CH=CH)-phenyl- substituted with R$^{33}$;
2-((MeOC=O)CH=CH)-phenyl- substituted with R$^{33}$;
2-(methyl)-phenyl- substituted with R$^{33}$;
2-(ethyl)-phenyl- substituted with R$^{33}$;
2-(i-propyl)-phenyl- substituted with R$^{33}$;
2-(F$_3$C)-phenyl- substituted with R$^{33}$;
2-(NC)-phenyl- substituted with R$^{33}$;
2-(H$_3$CO)-phenyl- substituted with R$^{33}$;
2-(fluoro)-phenyl- substituted with R$^{33}$;
2-(chloro)-phenyl- substituted with R$^{33}$;
3-(NC)-phenyl- substituted with R$^{33}$;
3-(H$_3$CO)-phenyl- substituted with R$^{33}$;
3-(fluoro)-phenyl- substituted with R$^{33}$;
3-(chloro)-phenyl- substituted with R$^{33}$;
4-(NC)-phenyl- substituted with R$^{33}$;
4-(fluoro)-phenyl- substituted with R$^{33}$;
4-(chloro)-phenyl- substituted with R$^{33}$;
4-(H$_3$CS)-phenyl- substituted with R$^{33}$;
4-(H$_3$CO)-phenyl- substituted with R$^{33}$;
4-(ethoxy)-phenyl- substituted with R$^{33}$;
4-(i-propoxy)-phenyl- substituted with R$^{33}$;
4-(i-butoxy)-phenyl- substituted with R$^{33}$;
4-(H$_3$CCH$_2$CH$_2$C(=O))-phenyl- substituted with R$^{33}$;
4-((H$_3$C)$_2$CHC(=O))-phenyl- substituted with R$^{33}$;
4-(H$_3$CCH$_2$C(=O))-phenyl- substituted with R$^{33}$;
4-(H$_3$CC(=O))-phenyl- substituted with R$^{33}$;
4-(H$_3$CCH$_2$CH$_2$CH(OH))-phenyl- substituted with R$^{33}$;
4-((H$_3$C)$_2$CHCH(OH))-phenyl- substituted with R$^{33}$;
4-(H$_3$CCH$_2$CH(OH))-phenyl- substituted with R$^{33}$;
4-(H$_3$CCH(OH))-phenyl- substituted with R$^{33}$;
4-(cyclopropyloxy)-phenyl- substituted with R$^{33}$;
4-(cyclobutyloxy)-phenyl- substituted with R$^{33}$; and
4-(cyclopentyloxy)-phenyl- substituted with R$^{33}$;

R¹³ is H, methyl, or ethyl;

alternatively, R¹² and R¹³ join to form a 5- or 6-membered ring selected from pyrrolyl, pyrrolidinyl, imidazolyl, piperidinyl, piperizinyl, methylpiperizinyl, and morpholinyl;

alternatively, R¹² and R¹³ when attached to N may be combined to form a 9- or 10-membered bicyclic heterocyclic ring system containing from 1–3 heteroatoms selected from the group consisting of N, O, and S; wherein said bicyclic heterocyclic ring system is selected from indolyl, indolinyl, indazolyl, benzimidazolyl, benzimidazolinyl, and benztriazolyl; wherein said bicyclic heterocyclic ring system is substituted with 0–1 R¹⁶;

R¹⁶, at each occurrence, is independently selected from H, OH, F, Cl, CN, NO₂, methyl, ethyl, methoxy, ethoxy, trifluoromethyl, and trifluoromethoxy; and R³¹, at each occurrence, is independently selected from H, —OH, F, Cl, —CF₃, —OCF₃, methyl, ethyl, methyl-C(=O)—, ethyl-C(=O)—, methoxy, ethoxy, methylthio-, ethylthio-, methyl-S(=O)—, ethyl-S(=O)—, methyl-SO₂—, and ethyl-SO₂—;

R³³, at each occurrence, is independently selected from H, F, Cl, —CH₃, —OCH₃, —CF₃, —OCF₃, —CN, and —NO₂.

3. A compound of claim 2 of formula (I) wherein:

R^A is selected from
phenyl-NH—, (1-naphthyl)-NH—,
(2-naphthyl)-NH—, (2-[1,1'-biphenyl])-NH—,
(3-[1,1'-biphenyl])-NH—, (4-[1,1'-biphenyl])-NH—,
(2-F-phenyl)-NH—, (2-Cl-phenyl)-NH—,
(2-CF₃-phenyl)-NH—, (2-CH₃-phenyl)-NH—,
(2-OMe-phenyl)-NH—, (2-CN-phenyl)-NH—,
(2-OCF₃-phenyl)-NH—, (2-SMe-phenyl)-NH—,
(3-F-phenyl)-NH—, (3-Cl-phenyl)-NH—,
(3-CF₃-phenyl)-NH—, (3-CH₃-phenyl)-NH—,
(3-OMe-phenyl)-NH—, (3-CN-phenyl)-NH—,
(3-OCF₃-phenyl)-NH—, (3-SMe-phenyl)-NH—,
(4-F-phenyl)-NH—, (4-Cl-phenyl)-NH—,
(4-CF₃-phenyl)-NH—, (4-CH₃-phenyl)-NH—,
(4-OMe-phenyl)-NH—, (4-CN-phenyl)-NH—,
(4-OCF₃-phenyl)-NH—, (4-SMe-phenyl)-NH—,
(2,3-diCl-phenyl)-NH—, (2,4-diCl-phenyl)-NH—,
(2,5-diCl-phenyl)-NH—, (2,6-diCl-phenyl)-NH—,
(3,4-diCl-phenyl)-NH—, (3,5-diCl-phenyl)-NH—,
(2,3-diF-phenyl)-NH—, (2,4-diF-phenyl)-NH—,
(2,5-diF-phenyl)-NH—, (2,6-diF-phenyl)-NH—,
(3,4-diF-phenyl)-NH—, (3,5-diF-phenyl)-NH—,
(2,3-diCH₃-phenyl)-NH—, (2,4-diCH₃-phenyl)-NH—,
(2,5-diCH₃-phenyl)-NH—, (2,6-diCH₃-phenyl)-NH—,
(3,4-diCH₃-phenyl)-NH—, (3,5-diCH₃-phenyl)-NH—,
(2,3-diCF₃-phenyl)-NH—, (2,4-diCF₃-phenyl)-NH—,
(2,5-diCF₃-phenyl)-NH—, (2,6-diCF₃-phenyl)-NH—,
(3,4-diCF₃-phenyl)-NH—, (3,5-diCF₃-phenyl)-NH—,
(2,3-diOMe-phenyl)-NH—, (2,4-diOMe-phenyl)-NH—,
(2,5-diOMe-phenyl)-NH—, (2,6-diOMe-phenyl)-NH—,
(3,4-diOMe-phenyl)-NH—, (3,5-diOMe-phenyl)-NH—,
(2-F-3-Cl-phenyl)-NH—, (2-F-4-Cl-phenyl)-NH—,
(2-F-5-Cl-phenyl)-NH—, (2-F-6-Cl-phenyl)-NH—,
(2-F-3-CH₃-phenyl)-NH—, (2-F-4-CH₃-phenyl)-NH—,
(2-F-5-CH₃-phenyl)-NH—, (2-F-6-CH₃-phenyl)-NH—,
(2-F-3-CF₃-phenyl)-NH—, (2-F-4-CF₃-phenyl)-NH—,
(2-F-5-CF₃-phenyl)-NH—, (2-F-6-CF₃-phenyl)-NH—,
(2-F-3-OMe-phenyl)-NH—, (2-F-4-OMe-phenyl)-NH—,
(2-F-5-OMe-phenyl)-NH—, (2-F-6-OMe-phenyl)-NH—,
(2-Cl-3-F-phenyl)-NH—, (2-Cl-4-F-phenyl)-NH—,
(2-Cl-5-F-phenyl)-NH—, (2-Cl-6-F-phenyl)-NH—,
(2-Cl-3-CH₃-phenyl)-NH—, (2-Cl-4-CH₃-phenyl)-NH—,
(2-Cl-5-CH₃-phenyl)-NH—, (2-Cl-6-CH₃-phenyl)-NH—,
(2-Cl-3-CF₃-phenyl)-NH—, (2-Cl-4-CF₃-phenyl)-NH—,
(2-Cl-5-CF₃-phenyl)-NH—, (2-Cl-6-CF₃-phenyl)-NH—,
(2-Cl-3-OMe-phenyl)-NH—, (2-Cl-4-OMe-phenyl)-NH—,
(2-Cl-5-OMe-phenyl)-NH—, (2-Cl-6-OMe-phenyl)-NH—,
(2-CH₃-3-F-phenyl)-NH—, (2-CH₃-4-F-phenyl)-NH—,
(2-CH₃-5-F-phenyl)-NH—, (2-CH₃-6-F-phenyl)-NH—,
(2-CH₃-3-Cl-phenyl)-NH—, (2-CH₃-4-Cl-phenyl)-NH—,
(2-CH₃-5-Cl-phenyl)-NH—, (2-CH₃-6-C₁-phenyl)-NH—,
(2-CH₃-3-CF₃-phenyl)-NH—, (2-CH₃-4-CF₃-phenyl)-NH—,
(2-CH₃-5-CF₃-phenyl)-NH—, (2-CH₃-6-CF₃-phenyl)-NH—,
(2-CH₃-3-OMe-phenyl)-NH—, (2-CH₃-4-OMe-phenyl)-NH—,
(2-CH₃-5-OMe-phenyl)-NH—, (2-CH₃-6-OMe-phenyl)-NH—,
(2-CF₃-3-F-phenyl)-NH—, (2-CF₃-4-F-phenyl)-NH—,
(2-CF₃-5-F-phenyl)-NH—, (2-CF₃-6-F-phenyl)-NH—,
(2-CF₃-3-Cl-phenyl)-NH—, (2-CF₃-4-Cl-phenyl)-NH—,
(2-CF₃-5-Cl-phenyl)-NH—, (2-CF₃-6-Cl-phenyl)-NH—,
(2-CF₃-3-CH₃-phenyl)-NH—, (2-CF₃-4-CH₃-phenyl)-NH—,
(2-CH₃-5-F₃-phenyl)-NH—, (2-CF₃-6-CH₃-phenyl)-NH—,
(2-CF₃-3-OMe-phenyl)-NH—, (2-CF₃-4-OMe-phenyl)-NH—,
(2-CF₃-5-OMe-phenyl)-NH—, (2-CF₃-6-OMe-phenyl)-NH—,
(2-OMe-3-F-phenyl)-NH—, (2-OMe-4-F-phenyl)-NH—,
(2-OMe-5-F-phenyl)-NH—, (2-OMe-6-F-phenyl)-NH—,
(2-OMe-3-Cl-phenyl)-NH—, (2-OMe-4-Cl-phenyl)-NH—,
(2-OMe-5-Cl-phenyl)-NH—, (2-OMe-6-Cl-phenyl)-NH—,
(2-OMe-3-CH₃-phenyl)-NH—, (2-OMe-4-CH₃-phenyl)-NH—,
(2-OMe-5-CH₃-phenyl)-NH—, (2-OMe-6-CH₃-phenyl)-NH—,
(2-OMe-3-CF₃-phenyl)-NH—, (2-OMe-4-CF₃-phenyl)-NH—, (2-OMe-5-CF$_3$-phenyl)-NH—, (2-OMe-6-CF$_3$-phenyl)-NH—,
(3-CF$_3$-4-Cl-phenyl)-NH—, (3-CF$_3$-4-C(O)CH$_3$-phenyl)-NH—, (2,3,5-triCl-phenyl)-NH—, (3-CH$_3$-4-CO$_2$Me-phenyl)-NH—, and
(3-CHO-4-OMe-phenyl)-NH—;

R$^B$ is selected from
2-chlorophenyl, 2-fluorophenyl, 2-bromophenyl,
2-cyanophenyl, 2-methylphenyl, 2-trifluoromethylphenyl,
2-methoxyphenyl, 2-trifluoromethoxyphenyl,
3-chlorophenyl, 3-fluorophenyl, 3-bromophenyl,
3-cyanophenyl, 3-methylphenyl, 3-ethylphenyl,
3-propylphenyl, 3-isopropylphenyl, 3-butylphenyl,
3-trifluoromethylphenyl, 3-methoxyphenyl,
3-isopropoxyphenyl, 3-trifluoromethoxyphenyl,
3-thiomethoxyphenyl,
4-chlorophenyl, 4-fluorophenyl, 4-bromophenyl,
4-cyanophenyl, 4-methylphenyl, 4-ethylphenyl,
4-propylphenyl, 4-isopropylphenyl, 4-butylphenyl,
4-trifluoromethylphenyl, 4-methoxyphenyl,
4-isopropoxyphenyl, 4-trifluoromethoxyphenyl,
4-thiomethoxyphenyl,
2,3-dichlorophenyl, 2,3-difluorophenyl,
2,3-dimethylphenyl, 2,3-ditrifluoromethylphenyl,
2,3-dimethoxyphenyl, 2,3-ditrifluoromethoxyphenyl,
2,4-dichlorophenyl, 2,4-difluorophenyl,
2,4-dimethylphenyl, 2,4-ditrifluoromethylphenyl,
2,4-dimethoxyphenyl, 2,4-ditrifluoromethoxyphenyl,
2,5-dichlorophenyl, 2,5-difluorophenyl,
2,5-dimethylphenyl, 2,5-ditrifluoromethylphenyl,
2,5-dimethoxyphenyl, 2,5-ditrifluoromethoxyphenyl,
2,6-dichlorophenyl, 2,6-difluorophenyl,
2,6-dimethylphenyl, 2,6-ditrifluoromethylphenyl,
2,6-dimethoxyphenyl, 2,6-ditrifluoromethoxyphenyl,
3,4-dichlorophenyl, 3,4-difluorophenyl,
3,4-dimethylphenyl, 3,4-ditrifluoromethylphenyl,
3,4-dimethoxyphenyl, 3,4-ditrifluoromethoxyphenyl,
2,4,6-trichlorophenyl, 2,4,6-trifluorophenyl,
2,4,6-trimethylphenyl, 2,4,6-tritrifluoromethylphenyl,
2,4,6-trimethoxyphenyl, 2,4,6-tritrifluoromethoxyphenyl,
2-chloro-4-CF$_3$-phenyl, 2-fluoro-3-chloro-phenyl,
2-chloro-4-CF$_3$-phenyl, 2-chloro-4-methoxy-phenyl,
2-methoxy-4-isopropyl-phenyl, 2-CF$_3$-4-methoxy-phenyl,
2-methyl-4-methoxy-5-fluoro-phenyl,
2-methyl-4-methoxy-phenyl, 2-chloro-4-CF$_3$O-phenyl,
2,4,5-trimethyl-phenyl, 2-methyl-4-chloro-phenyl,
4-acetylphenyl, 3-acetamidophenyl, 2-naphthyl;
2-Me-5-F-phenyl, 2-F-5-Me-phenyl, 2-MeO-5-F-phenyl,
2-Me-3-Cl-phenyl, 3-NO$_2$-phenyl, 2-NO$_2$-phenyl,
2-Cl-3-Me-phenyl, 2-Me-4-EtO-phenyl, 2-Me-4-F-phenyl,
2-Cl-6-F-phenyl, 2-Cl-4-(CHF$_2$)O-phenyl,
2,4-diMeO-6-F-phenyl, 2-CF$_3$-6-F-phenyl,
2-MeS-phenyl, 2,6-diCl-4-MeO-phenyl,
2,3,4-triF-phenyl, 2,6-diF-4-Cl-phenyl,
2,3,4,6-tetraF-phenyl, 2,3,4,5,6-pentaF-phenyl,
2-CF$_3$-4-EtO-phenyl, 2-CF$_3$-4-iPrO-phenyl,
2-CF$_3$-4-Cl-phenyl, 2-CF$_3$-4-F-phenyl, 2-Cl-4-EtO-phenyl,
2-Cl-4-iPrO-phenyl, 2-Et-4-MeO-phenyl,
2-CHO-4-MeO-phenyl, 2-CH$_3$CH(OH)-4-MeO-phenyl,
2-CH$_3$CH(OH)-4-F-phenyl, 2-CH$_3$CH(OH)-4-Cl-phenyl,
2-CH$_3$CH(OH)-4-Me-phenyl, 2-CH$_3$CH(OMe)-4-MeO-phenyl,
2-CH$_3$C(=O)-4-MeO-phenyl, 2-CH$_3$C(=O)-4-F-phenyl,
2-CH$_3$C(=O)-4-Cl-phenyl, 2-CH$_3$C(=O)-4-Me-phenyl,
2-H$_2$C(OH)-4-MeO-phenyl, 2-H$_2$C(OMe)-4-MeO-phenyl,
2-H$_3$CCH$_2$CH(OH)-4-MeO-phenyl, 2-H$_3$CCH$_2$C(=O)-4-MeO-phenyl,
2-CH$_3$CO$_2$CH$_2$CH$_2$-4-MeO-phenyl,
(Z)-2-HOCH$_2$CH=CH-4-MeO-phenyl,
(E)-2-HOCH$_2$CH=CH-4-MeO-phenyl,
(Z)-2-CH$_3$CO$_2$CH=CH-4-MeO-phenyl,
(E)-2-CH$_3$CO$_2$CH=CH-4-MeO-phenyl,
2-CH$_3$OCH$_2$CH$_2$-4-MeO-phenyl,
2-F-4-MeO-phenyl, 2-Cl-4-F-phenyl,
cyclohexyl, cyclopentyl, cyclohexylmethyl,
benzyl, 2-F-benzyl, 3-F-benzyl, 4-F-benzyl,
3-MeO-benzyl, 3-OH-benzyl, 2-MeO-benzyl,
2-OH-benzyl, 2-MeOC(=O)-3-MeO-phenyl,
2-Me-4-CN-phenyl, 2-Me-3-CN-phenyl,
2-Me-4-MeS-phenyl, 2-CF$_3$-4-CN-phenyl,
2-CHO-phenyl, 3-CHO-phenyl, 2-HOCH$_2$-phenyl,
3-HOCH$_2$-phenyl, 3-MeOCH$_2$-phenyl,
3-Me$_2$NCH$_2$-phenyl, 3-CN-4-F-phenyl,
2-Me-4-H$_2$NCO-phenyl, 2-Me-4-MeOC(=O)-phenyl,
3-H$_2$NCO-4-F-phenyl, 2-Me$_2$NCH$_2$-4-MeO-phenyl-,
2-Me-4-CH$_3$C(=O)-phenyl,
phenyl-NH—, (1-naphthyl)-NH—,
(2-naphthyl)-NH—, (2-[1,1'-biphenyl])-NH—,
(3-[1,1'-biphenyl])-NH—, (4-[1,1'-biphenyl])-NH—,
(2-F-phenyl)-NH—, (2-Cl-phenyl)-NH—,
(2-CF$_3$-phenyl)-NH—, (2-CH$_3$-phenyl)-NH—,
(2-OMe-phenyl)-NH—, (2-CN-phenyl)-NH—,
(2-OCF$_3$-phenyl)-NH—, (2-SMe-phenyl)-NH—,
(3-F-phenyl)-NH—, (3-Cl-phenyl)-NH—,
(3-CF$_3$-phenyl)-NH—, (3-CH$_3$-phenyl)-NH—,
(3-OMe-phenyl)-NH—, (3-CN-phenyl)-NH—,
(3-OCF$_3$-phenyl)-NH—, (3-SMe-phenyl)-NH—,
(4-F-phenyl)-NH—, (4-Cl-phenyl)-NH—,
(4-CF$_3$-phenyl)-NH—, (4-CH$_3$-phenyl)-NH—,
(4-OMe-phenyl)-NH—, (4-CN-phenyl)-NH—,
(4-OCF$_3$-phenyl)-NH—, (4-SMe-phenyl)-NH—,
(2,3-diCl-phenyl)-NH—, (2,4-diCl-phenyl)-NH—,
(2,5-diCl-phenyl)-NH—, (2,6-diCl-phenyl)-NH—,
(3,4-diCl-phenyl)-NH—, (3,5-diCl-phenyl)-NH—,
(2,3-diF-phenyl)-NH—, (2,4-diF-phenyl)-NH—,
(2,5-diF-phenyl)-NH—, (2,6-diF-phenyl)-NH—,
(3,4-diF-phenyl)-NH—, (3,5-diF-phenyl)-NH—,
(2,3-diCH$_3$-phenyl)-NH—, (2,4-diCH$_3$-phenyl)-NH—,
(2,5-diCH$_3$-phenyl)-NH—, (2,6-diCH$_3$-phenyl)-NH—,
(3,4-diCH$_3$-phenyl)-NH—, (3,5-diCH$_3$-phenyl)-NH—,
(2,3-diCF$_3$-phenyl)-NH—, (2,4-diCF$_3$-phenyl)-NH—,
(2,5-diCF$_3$-phenyl)-NH—, (2,6-diCF$_3$-phenyl)-NH—,
(3,4-diCF$_3$-phenyl)-NH—, (3,5-diCF$_3$-phenyl)-NH—,
(2,3-diOMe-phenyl)-NH—, (2,4-diOMe-phenyl)-NH—,
(2,5-diOMe-phenyl)-NH—, (2,6-diOMe-phenyl)-NH—,
(3,4-diOMe-phenyl)-NH—, (3,5-diOMe-phenyl)-NH—,
(2-F-3-Cl-phenyl)-NH—, (2-F-4-Cl-phenyl)-NH—,
(2-F-5-Cl-phenyl)-NH—, (2-F-6-Cl-phenyl)-NH—,
(2-F-3-CH$_3$-phenyl)-NH—, (2-F-4-CH$_3$-phenyl)-NH—,
(2-F-5-CH$_3$-phenyl)-NH—, (2-F-6-CH$_3$-phenyl)-NH—, (2-F-3-CF₃-phenyl)-NH—, (2-F-4-CF₃-phenyl)-NH—,
(2-F-5-CF₃-phenyl)-NH—, (2-F-6-CF₃-phenyl)-NH—,
(2-F-3-OMe-phenyl)-NH—, (2-F-4-OMe-phenyl)-NH—,
(2-F-5-OMe-phenyl)-NH—, (2-F-6-OMe-phenyl)-NH—,
(2-Cl-3-F-phenyl)-NH—, (2-Cl-4-F-phenyl)-NH—,
(2-Cl-5-F-phenyl)-NH—, (2-Cl-6-F-phenyl)-NH—,
(2-Cl-3-CH₃-phenyl)-NH—, (2-Cl-4-CH₃-phenyl)-NH—,
(2-Cl-5-CH₃-phenyl)-NH—, (2-Cl-6-CH₃-phenyl)-NH—,
(2-Cl-3-CF₃-phenyl)-NH—, (2-Cl-4-CF₃-phenyl)-NH—,
(2-Cl-5-CF₃-phenyl)-NH—, (2-Cl-6-CF₃-phenyl)-NH—,
(2-Cl-3-OMe-phenyl)-NH—, (2-Cl-4-OMe-phenyl)-NH—,
(2-Cl-5-OMe-phenyl)-NH—, (2-Cl-6-OMe-phenyl)-NH—,
(2-CH₃-3-F-phenyl)-NH—, (2-CH₃-4-F-phenyl)-NH—,
(2-CH₃-5-F-phenyl)-NH—, (2-CH₃-6-F-phenyl)-NH—,
(2-CH₃-3-Cl-phenyl)-NH—, (2-CH₃-4-Cl-phenyl)-NH—,
(2-CH₃-5-Cl-phenyl)-NH—, (2-CH₃-6-Cl-phenyl)-NH—,
(2-CH₃-3-CF₃-phenyl)-NH—, (2-CH₃-4-CF₃-phenyl)-NH—,
(2-CH₃-5-CF₃-phenyl)-NH—, (2-CH₃-6-CF₃-phenyl)-NH—,
(2-CH₃-3-O=e-phenyl)-NH—, (2-CH₃-4-OMe-phenyl)-NH—,
(2-CH₃-5-OMe-phenyl)-NH—, (2-CH₃-6-OMe-phenyl)-NH—,
(2-CF₃-3-F-phenyl)-NH—, (2-CF₃-4-F-phenyl)-NH—,
(2-CF₃-5-F-phenyl)-NH—, (2-CF₃-6-F-phenyl)-NH—,
(2-CF₃-3-Cl-phenyl)-NH—, (2-CF₃-4-Cl-phenyl)-NH—,
(2-CF₃-5-Cl-phenyl)-NH—, (2-CF₃-6-Cl-phenyl)-NH—,
(2-CF₃-3-CH₃-phenyl)-NH—, (2-CF₃-4-CH₃-phenyl)-NH—,
(2-CH₃-5-CF₃-phenyl)-NH—, (2-CF₃-6-CH₃-phenyl)-NH—,
(2-CF₃-3-OMe-phenyl)-NH—, (2-CF₃-4-OMe-phenyl)-NH—,
(2-CF₃-5-OMe-phenyl)-NH—, (2-CF₃-6-Ome-phenyl)-NH—,
(2-OMe-3-F-phenyl)-NH—, (2-OMe-4-F-phenyl)-NH—,
(2-OMe-5-F-phenyl)-NH—, (2-OMe-6-F-phenyl)-NH—,
(2-OMe-3-Cl-phenyl)-NH—, (2-OMe-4-Cl-phenyl)-NH—,
(2-OMe-5-Cl-phenyl)-NH—, (2-OMe-6-Cl-phenyl)-NH—,
(2-OMe-3-CH₃-phenyl)-NH—, (2-OMe-4-CH₃-phenyl)-NH—,
(2-OMe-5-CH₃-phenyl)-NH—, (2-OMe-6-CH₃-phenyl)-NH—,
(2-OMe-3-CF₃-phenyl)-NH—, (2-OMe-4-CF₃-phenyl)-NH—,
(2-OMe-5-CF₃-phenyl)-NH—, (2-OMe-6-CF₃-phenyl)-NH—
(3-CF₃-4-Cl-phenyl)-NH—, (3-CF₃-4-C(O)CH₃-phenyl)-NH—, (2,3,5-triCl-phenyl)-NH—, (3-CH₃-4-CO₂Me-phenyl)-NH—, and
(3-CHO-4-OMe-phenyl)-NH—; and $R^{31}$, at each occurrence, is independently selected from H, —OH, F, Cl, —CF₃, —OCF₃, methyl, methyl-C(=O)—, methoxy, methylthio-, methyl-S(=O)—, and methyl-SO₂—.

4. A pharmaceutical composition comprising a pharmaceutically acceptable carrier and a therapeutically effective amount of a compound of claim 1, or a pharmaceutically acceptable salt thereof.

5. A pharmaceutical composition comprising a pharmaceutically acceptable carrier and a therapeutically effective amount of a compound of claim 2, or a pharmaceutically acceptable salt thereof.

6. A pharmaceutical composition comprising a pharmaceutically acceptable carrier and a therapeutically effective amount of a compound of claim 3, or a pharmaceutically acceptable sait thereof.

7. A method for treating a human suffering from a disorder associated with 5HT2C receptor modulation comprising administering to a patient in need thereof a therapeutically effective amount of a compound of claim 1, or a pharmaceutically acceptable salt thereof.

8. A method for treating a human suffering from a disorder associated with 5HT2C receptor modulation comprising administering to a patient in need thereof a therapeutically effective amount of a compound of claim 2, or a pharmaceutically acceptable salt thereof.

9. A method for treating a human suffering from a disorder associated with 5HT2C receptor modulation comprising administering to a patient in need thereof a therapeutically effective amount of a compound of claim 3, or a pharmaceutically acceptable salt thereof.

10. A method of claim 7 for treating a human suffering from a disorder associated with 5HT2C receptor modulation wherein the compound is a 5HT2C agonist.

11. A method of claim 8 for treating a human suffering from a disorder associated with 5HT2C receptor modulation wherein the compound is a 5HT2C agonist.

12. A method of claim 9 for treating a human suffering from a disorder associated with 5HT2C receptor modulation wherein the compound is a 5HT2C agonist.

13. A method for treating obesity comprising administering to a patient in need thereof a therapeutically effective amount of a compound of claim 1, or a pharmaceutically acceptable salt thereof.

14. A method for treating obesity comprising administering to a patient in need thereof a therapeutically effective amount of a compound of claim 2, or a pharmaceutically acceptable salt thereof.

15. A method for treating obesity comprising administering to a patient in need thereof a therapeutically effective amount of a compound of claim 3, or a pharmaceutically acceptable salt thereof.

\* \* \* \* \*